United States Patent
Ishioka et al.

(10) Patent No.: US 12,102,694 B2
(45) Date of Patent: Oct. 1, 2024

(54) RADIOLABELED COMPOUND PRODUCING METHOD AND PRODUCING APPARATUS, RADIOLABELED COMPOUND AND RADIOISOTOPE PRODUCING APPARATUS

(71) Applicant: NATIONAL INSTITUTES FOR QUANTUM SCIENCE AND TECHNOLOGY, Chiba (JP)

(72) Inventors: Noriko Ishioka, Gunma (JP); Hiroo Kondo, Aomori (JP); Shigeki Watanabe, Gunma (JP)

(73) Assignee: NATIONAL INSTITUTES FOR QUANTUM SCIENCE AND TECHNOLOGY, Chiba (JP)

( * ) Notice: Subject to any disclaimer, the term of this patent is extended or adjusted under 35 U.S.C. 154(b) by 629 days.

(21) Appl. No.: 17/442,715

(22) PCT Filed: Jan. 23, 2020

(86) PCT No.: PCT/JP2020/002329
§ 371 (c)(1),
(2) Date: Sep. 24, 2021

(87) PCT Pub. No.: WO2020/202726
PCT Pub. Date: Oct. 8, 2020

(65) Prior Publication Data
US 2022/0184238 A1    Jun. 16, 2022

(30) Foreign Application Priority Data

Mar. 29, 2019   (JP) .................... 2019-068102

(51) Int. Cl.
*A61K 51/02*   (2006.01)
*C07K 1/13*   (2006.01)
*G21G 1/04*   (2006.01)

(52) U.S. Cl.
CPC ............. *A61K 51/02* (2013.01); *C07K 1/13* (2013.01); *G21G 1/04* (2013.01); *C07B 2200/05* (2013.01)

(58) Field of Classification Search
CPC ............ A61K 51/02; C07K 1/13; G21G 1/04; C07B 2200/05
(Continued)

(56) References Cited

U.S. PATENT DOCUMENTS

2011/0165070 A1   7/2011  Stephens et al.
2011/0286565 A1   11/2011 Tsang
(Continued)

FOREIGN PATENT DOCUMENTS

JP   2013-511046 A   3/2013
JP   2014-196997 A   10/2014
(Continued)

OTHER PUBLICATIONS

Wilbur et al., "Reagents for Astatination of Biomolecules. 2. Conjugation of Anionic Boron Cage Pendant Groups to a Protein Provides a Method for Direct Labeling That is Stable to in Vivo Deastatination", Bioconjugate Chem., vol. 18, 2007, pp. 1226-1240.
(Continued)

*Primary Examiner* — Anita Nassiri-Motlagh
(74) *Attorney, Agent, or Firm* — MARSHALL, GERSTEIN & BORUN LLP

(57) ABSTRACT

The problem to be solved by the present invention is to provide a technique that allows producing a novel radiolabeled compound. The invention is a method for producing a radiolabeled compound, the method including the steps of: irradiating an alloy of a target substance with a radiation beam, to generate two or more radioisotopes from the alloy, and allowing the two or more radioisotopes to migrate into a gas; a step of generating an intermediate label by allowing
(Continued)

a first radioisotope, from among the two or more radioisotopes having migrated into the gas, to react with a label precursor; and a step of generating a final label by allowing a second radioisotope different from the first radioisotope, from among the two or more radioisotopes having migrated into the gas, to react with the intermediate label.

6 Claims, 12 Drawing Sheets

(58) Field of Classification Search
USPC .......................................................... 423/2
See application file for complete search history.

(56) References Cited

U.S. PATENT DOCUMENTS

| | | |
|---|---|---|
| 2014/0286862 A1 | 9/2014 | Strand et al. |
| 2015/0079000 A1 | 3/2015 | Chezal et al. |
| 2019/0051426 A1 | 2/2019 | Murakami et al. |

FOREIGN PATENT DOCUMENTS

| | | |
|---|---|---|
| JP | 2014-530898 A | 11/2014 |
| JP | 2015-147767 A | 8/2015 |
| JP | 2018-502054 A | 1/2018 |
| WO | WO-2006/074960 A1 | 7/2006 |
| WO | WO-2012/039038 A1 | 3/2012 |
| WO | WO-2013/061083 A2 | 5/2013 |
| WO | WO-2016/064379 A1 | 4/2016 |
| WO | WO-2017/183697 A1 | 10/2017 |

OTHER PUBLICATIONS

Tall et al., "Volatile Elements Production Rates in a Proton-irradiated Molten Lead-bismuth Target", International Conference on Nuclear Data for Science and Technology 2007, Article No. 281, Mar. 21, 2008, pp. 1069-1072.
Turkington, et al., "Measuring astatine-211 distributions with SPECT", Phys. Med. Biol., 1993, 38, pp. 1121-1130.
Nagao, et al., "Astatine-211 imaging by a Compton camera for targeted radiotherapy", Applied Radiation and Isotopes, 2018, 139, pp. 238-243.
Search Report in International Application No. PCT/JP2020/002329 dated Mar. 24, 2020, 3 pages.
Extended European Search Report in EP Application No. 20782782.5 dated Nov. 21, 2022, 8 pages.

*FIG. 11*

|  | GROUP 14 | | GROUP 15 | | GROUP 16 | | GROUP 17 | |
|---|---|---|---|---|---|---|---|---|
|  | Ge | | As | | Se | | Br | |
| Pressure | Temp | | Temp | | Temp | | Temp | |
| Pa | °C | K | °C | K | °C | K | °C | K |
| 1.0.E+00 | 1371 | 1644 | 280 | 553 | 227 | 500 | -88 | 185 |
| 1.0.E+01 | 1541 | 1814 | 323 | 596 | 279 | 552 | -72 | 201 |
| 1.0.E+02 | 1750 | 2023 | 373 | 646 | 344 | 617 | -53 | 220 |
| 1.0.E+03 | 2014 | 2287 | 433 | 706 | 431 | 704 | -29 | 244 |
| 1.0.E+04 | 2360 | 2633 | 508 | 781 | 540 | 813 | 3 | 276 |
| 1.0.E+05 | 2741 | 3014 | 601 | 874 | 685 | 958 | 59 | 332 |
|  | Sn | | Sb | | Te | | I | |
| Pressure | Temp | | Temp | | Temp | | Temp | |
| Pa | °C | K | °C | K | °C | K | °C | K |
| 1.0.E+00 | 1224 | 1497 | 534 | 807 |  |  | -13 | 260 |
| 1.0.E+01 | 1384 | 1657 | 603 | 876 |  |  | 9 | 282 |
| 1.0.E+02 | 1582 | 1855 | 738 | 1011 |  |  | 36 | 309 |
| 1.0.E+03 | 1834 | 2107 | 946 | 1219 |  |  | 69 | 342 |
| 1.0.E+04 | 2165 | 2438 | 1218 | 1491 | 769 | 1042 | 108 | 381 |
| 1.0.E+05 | 2620 | 2893 | 1585 | 1858 | 993 | 1266 | 184 | 457 |
|  | Pb | | Bi | | Po | | At | |
| Pressure | Temp | | Temp | | Temp | | Temp | |
| Pa | °C | K | °C | K | °C | K | °C | K |
| 1.0E+00 | 705 | 978 | 668 | 941 |  |  | 88 | 361 |
| 1.0E+01 | 815 | 1088 | 768 | 1041 |  |  | 119 | 392 |
| 1.0E+02 | 956 | 1229 | 892 | 1165 |  |  | 156 | 429 |
| 1.0E+03 | 1139 | 1412 | 1052 | 1325 | 573 | 846 | 202 | 475 |
| 1.0E+04 | 1387 | 1660 | 1265 | 1538 | 730 | 1003 | 258 | 531 |
| 1.0E+05 | 1754 | 2027 | 1562 | 1835 | 963 | 1236 | 334 | 607 |

RADIOLABELED COMPOUND PRODUCING METHOD AND PRODUCING APPARATUS, RADIOLABELED COMPOUND AND RADIOISOTOPE PRODUCING APPARATUS

TECHNICAL FIELD

The present invention relates to a radiolabeled compound producing method and producing apparatus, a radiolabeled compound and a radioisotope producing apparatus.

BACKGROUND ART

In recent years, RI (radioisotope) drugs have come to be actively used in the medical field, for instance in the treatment of cancer (see for example PTL 1 and NPL 1 to 3).

CITATION LIST

Patent Literature

[PTL 1] Japanese Patent Application Publication No. 2015-147767

Non Patent Literature

[NPL 1] T G Turkington, et al., "Measuring astatine-211 distributions with SPECT", Phys. Med. Biol., 1993, 38, 1121-1130

[NPL 2] Yuto Nagao, et al., "Astatine-211 imaging by a Compton camera for targeted radiotherapy", Applied Radiation and Isotopes, 2018, 139, 238-243

[NPL 3] D. Scott Wilbur, et al., "Reagents for Astatination of Biomolecules. 2. Conjugation of Anionic Boron Cage Pendant Groups to a Protein Provides a Method for Direct Labeling that is Stable to in Vivo Deastatination", Bioconjugate Chem. 2007, 18, 1226-1240

SUMMARY OF INVENTION

Technical Problem

For instance in RI therapeutic drugs administered for the purpose of treating cancer radiation emitted towards the exterior the body is very weak, and accordingly it is difficult to image the biodistribution of the RI therapeutic drugs through capture of radiation from outside the body. Therefore, means that have been tried to date for accurately grasping drug accumulation at a lesion site, so as to perform an appropriate treatment, include a first means, namely imaging of distribution upon administration of an RI drug for imaging, and a second means, namely imaging by capturing extremely weak radiation emitted from the RI therapeutic drug to the exterior of the body, using a high-sensitivity apparatus. In the first means, however, the biodistribution of the RI drug may vary when the radioisotope bound to a carrier varies, even for a same carrier; accordingly, distribution images obtained through administration of an RI drug for imaging are not necessarily identical to those of the distribution in the case of administration of an RI drug for treatment. In the second means, the ability of an apparatus for capturing and imaging, with high sensitivity, extremely weak radiation emitted from the RI therapeutic drug to the exterior of the body is not sufficient, and it thus difficult to obtain images of sufficiently high resolution.

Therefore, it is an object of the present invention to provide a technique that allows producing a novel radiolabeled compound.

Solution to Problem

In order to solve the above problem, the present invention strives to make it possible to produce a radiolabeled compound in which two or more radioisotopes are bound to a single carrier, through the use of two or more radioisotopes that are generated from an alloy of a target substance, by irradiating the alloy as a target substance with a radiation beam, and thereupon allowing the radioisotopes to migrate into a gas.

In further detail, the present invention is a method for producing a radiolabeled compound, the method including the steps of: irradiating an alloy as a target substance with a radiation beam, to generate two or more radioisotopes from the alloy, and allowing the two or more radioisotopes to migrate into a gas; generating an intermediate label by allowing a first radioisotope, from among the two or more radioisotopes having migrated into the gas, to react with a label precursor; and generating a final label by allowing a second radioisotope different from the first radioisotope, from among the two or more radioisotopes having migrated into the gas, to react with the intermediate label.

In the above producing method, an alloy as a target substance is irradiated with a radiation beam, and accordingly it becomes possible to generate two or more radioisotopes within a liquid target, and to generate a radiolabeled compound that is labeled with the two or more radioisotopes. In the above producing method, two or more radioisotopes can be generated simultaneously within a liquid target, through irradiation of the alloy as the target substance with a radiation beam; as a result, for instance the generated radioisotopes can bind quickly to a carrier, even in cases where the radioisotopes include a radioisotope of short half-life, and a radiolabeled compound can be generated that is labeled with the two or more radioisotopes.

In the present invention, the method for producing a radiolabeled compound may include the steps of: irradiating an alloy as a target substance with a radiation beam, to generate two or more radioisotopes from the alloy, and allowing the two or more radioisotopes to migrate into a gas; generating a first intermediate label by allowing a first radioisotope, from among the two or more radioisotopes having migrated into the gas, to react with a label precursor; generating a second intermediate label by allowing a second radioisotope different from the first radioisotope, from among the two or more radioisotopes having migrated into the gas, to react with a label precursor; and generating a final label by condensing the first intermediate label and the second intermediate label. Such a producing method as well allows generating a radiolabeled compound that is labeled with two or more radioisotopes.

The above method for producing a radiolabeled compound may further include a step of adjusting the temperature of the alloy so as to be a temperature at which both the first radioisotope and the second radioisotope evaporate, during irradiation with the radiation beam. In such a producing method at least two radioisotopes, namely a first radioisotope and a second radioisotope from among the multiple radioisotopes generated in the alloy, migrate into a gas, as a result of which the radioisotopes having migrated into the gas can be bound to a carrier.

The present invention can also be grasped from the aspect of a producing apparatus. For instance, the present invention may be an apparatus for producing a radiolabeled compound, the apparatus having: isotope generation means for irradiating an alloy as a target substance with a radiation beam, to generate two or more radioisotopes from the alloy, and allowing the two or more radioisotopes to migrate into a gas; a first generating unit which generates an intermediate label by allowing a first radioisotope, from among the two or more radioisotopes having migrated into the gas, to react with a label precursor; and a second generating unit which generates a final label by allowing a second radioisotope different from the first radioisotope, from among the two or more radioisotopes having migrated into the gas, to react with the intermediate label.

The present invention may have for instance isotope generation means for irradiating an alloy as a target substance with a radiation beam, to generate two or more radioisotopes from the alloy, and allowing the two or more radioisotopes to migrate into a gas; a third generating unit which generates a first intermediate label by allowing a first radioisotope, from among the two or more radioisotopes having migrated into the gas, to react with a label precursor; a fourth generating unit which generates a second intermediate label by allowing a second radioisotope different from the first radioisotope, from among the two or more radioisotopes having migrated into the gas, to react with a label precursor; and a fifth generating unit which generates a final label through condensation of the first intermediate label and the second intermediate label.

The present invention can also be grasped from the aspect of a radiolabeled compound. The present invention may be for instance a radiolabeled compound wherein two or more radioisotopes generated from an alloy of a target substance through irradiation of the alloy with a radiation beam, are bound to a single carrier.

The present invention may be a radiolabeled compound wherein astatine $^{211}$At and iodine $^{124}$I are bound to a single carrier.

The present invention can be grasped from the viewpoint of a radioisotope producing apparatus. For instance, the present invention may be an apparatus for producing a radioisotope, the apparatus having: a first container which stores a target substance; a second container which receives a liquid transferred from the first container; a beam introduction portion which is a passage of the radiation beam, for irradiating a target substance with a radiation beam within the first container; and an extraction unit which extracts, from a gas, a radioisotope generated in the first container by the radiation beam and which migrates into the gas in the second container, wherein the second container and the extraction unit are hermetically connected to each other so that the gas that contains the radioisotope is conducted therebetween.

Effects of Invention

The present invention allows producing a novel radiolabeled compound.

BRIEF DESCRIPTION OF DRAWINGS

FIG. 11 is a table illustrating examples of a relationship between saturated vapor pressure of elements in group 14, group 15, group 16 and group 17, and temperature.

DESCRIPTION OF EMBODIMENTS

Embodiments of the invention of the present application will be explained next. The embodiments illustrated below are implementations of the present invention and are not meant to limit the technical scope of the invention of the present application.

First Embodiment

Figure 1:
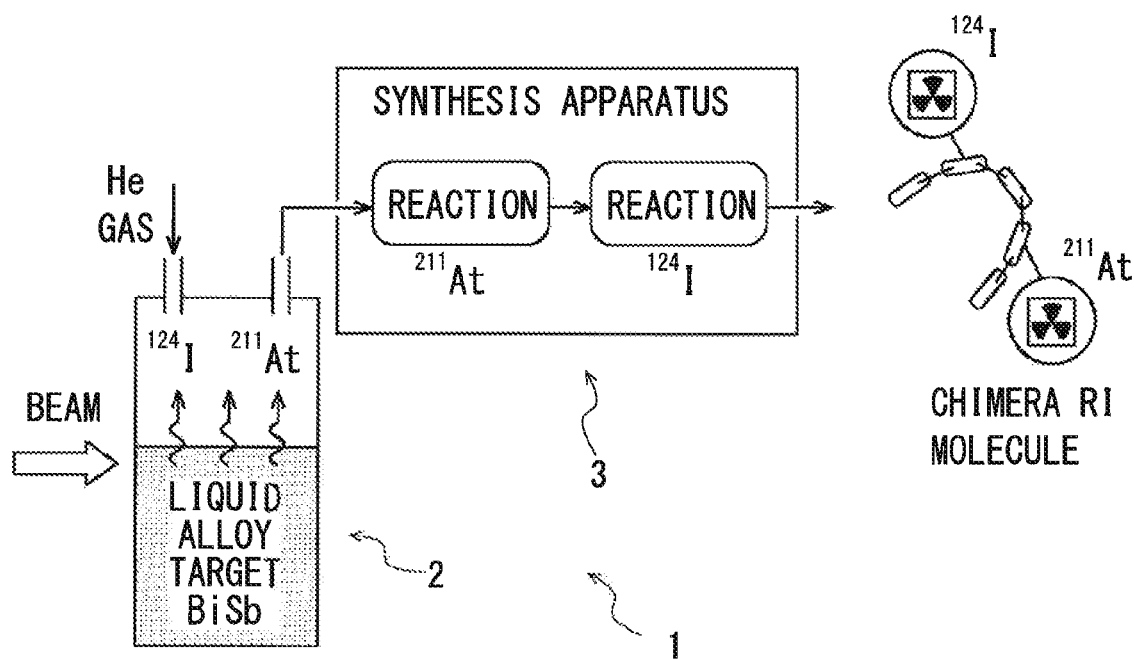
FIG. 1 is a diagram illustrating an example of a radiolabeled compound producing apparatus.

FIG. 1 is a diagram illustrating an example of a radiolabeled compound producing apparatus. The radiolabeled compound producing apparatus 1 is an apparatus in which an alloy as a target substance is irradiated with a radiation beam, to generate two or more radioisotopes, from the alloy, that are then allowed to migrate into a gas, whereupon the radioisotopes are combined with a label precursor. Accordingly, the radiolabeled compound producing apparatus 1 is provided with a radioisotope producing apparatus 2 that generates radioisotope and causes the radioisotopes to migrate into a gas, and a synthesis apparatus 3 which generates a chimera RI molecule by allowing the radioisotopes to react with a label precursor. In the present application the term chimera RI denotes a molecule resulting from binding of two or more radioisotopes to one molecule.

The term alloy denotes herein a mixture of two or more types of metals, the mixture being preferably at least solid or liquid at the temperature of the space in which the radioisotope producing apparatus 2 is installed. The term label precursor denotes for instance a substance, in an RI therapeutic drug, to which the radioisotopes are bound, and that is used as a carrier for transporting the radioisotope into the body.

FIG. 1 illustrates irradiation of an alloy of bismuth Bi and antimony Sb with a radiation beam to generate, from the alloy, astatine $^{211}$At and iodine $^{124}$I that are then allowed to migrate into a gas, whereupon the astatine $^{211}$At and the iodine $^{124}$I are allowed to react with a label precursor, to thereby generate a final label in the form of a chimera RI molecule. In the radiolabeled compound producing apparatus 1 of the present embodiment, two or more radioisotopes are generated simultaneously in the radioisotope producing apparatus 2 by one radiation beam, and the generated radioisotopes move at once into the synthesis apparatus 3 and are allowed to react with a label precursor. Accordingly, the radiolabeled compound producing apparatus 1 is suitable for synthesis of for instance a chimera RI molecule in which two or more halogen-based radioisotopes such as astatine $^{211}$At and iodine $^{124}$I are allowed to react with a label precursor. However, the radiolabeled compound producing apparatus 1 is not limited to generating such radiolabeled compounds.

Figure 2:
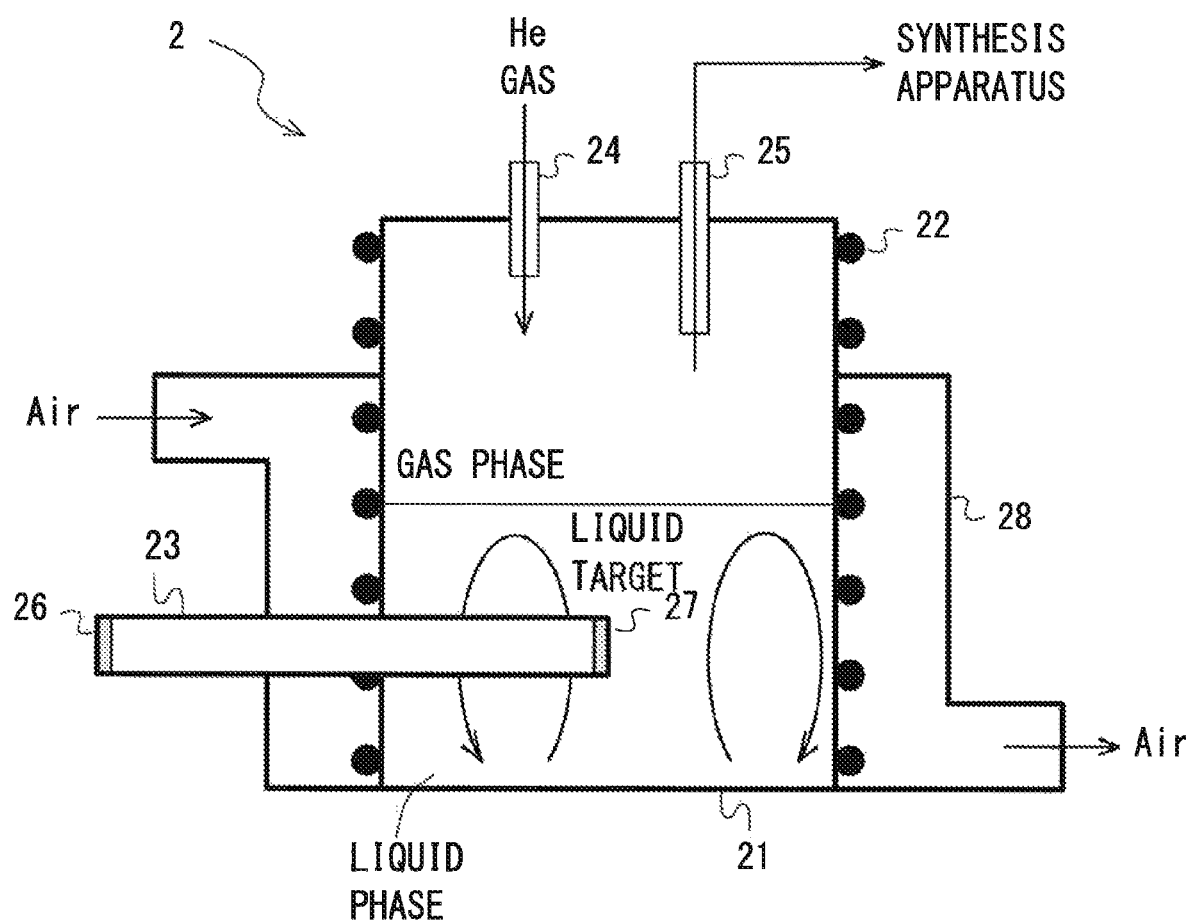
FIG. 2 is a diagram illustrating an example of a radioisotope producing apparatus.

FIG. 2 is a diagram illustrating an example of the radioisotope producing apparatus 2. The radioisotope producing apparatus 2 is provided with a crucible 21 that holds an alloy of a target substance, a heater 22 that heats up the alloy in the crucible 21, a beam port 23 for projecting a radiation beam to the alloy in the crucible 21, a gas introduction port 24 for introducing gas into the crucible 21, and a gas lead-out port 25 for leading, out of the crucible 21, the gas that is to be fed to the synthesis apparatus 3. Beam windows 26, 27 are provided in the beam port 23. A jacket 28 is provided with the crucible 21.

The crucible 21 is a container for storing, in the interior thereof, a target substance, and for melting at least part of the target-constituting substance. Preferably, the target substance is melted into a liquid, in the crucible 21. Accordingly, the crucible 21 is required to be at least heat-resistant enough to withstand a temperature of the melting point of the target substance. Therefore, for instance quartz, ceramics, metals and the like are suitably used as the material of such a crucible 21. The crucible 21 is sealed, and open portions other than the gas introduction port 24 and the gas lead-out port 25 are closed, at the time of irradiating with the radiation beam.

The heater 22 is a heating means for heating the interior of the crucible 21. The heater 22 heats up the interior of the crucible 21, to thereby heat up the target substance stored in the crucible 21. As a result, melting of the target substance is promoted, and part or the entirety of the target substance can be melted and liquefied. Various heating means, such as a micro sheath heater and others can be used as such a heater 22. During irradiating with the radiation beam, the irradiated portion generates heat on account of the energy from the radiation beam, and hence heating by the heater 22 may be unnecessary in some instances.

The jacket 28 is a cooling space disposed around the crucible 21. An inlet and an outlet of a coolant for cooling the crucible 21 are provided with the jacket 28, such that the jacket 28 can be cooled through introduction of the coolant into the jacket 28 via the inlet. Also, natural heat dissipation elicited through discontinuation of heating by the heater 22 can be expected to result in cooling of the crucible 21. The crucible 21 can however be cooled more quickly through introduction of a coolant into the jacket 28. Examples of the coolant that is introduced into the jacket 28 include for instance air in the room in which the radiolabeled compound producing apparatus 1 is installed, or a gas such as nitrogen gas, or liquid such as water, prepared for the purpose of cooling of the crucible 21. The manner in which the crucible 21 is cooled may involve for instance allowing a coolant to flow thus in the jacket 28; or alternatively, providing cooling fins on the surface of the crucible 21, or providing a thermoelectric conversion element such a Peltier element.

The beam port 23 is a tubular part running through a side wall portion of the crucible 21, and which forms a passage for allowing a radiation beam, outputted from a radiation beam generator disposed in the vicinity of the crucible 21, to strike into the crucible 21. Accordingly, the target substance stored in the crucible 21 is disposed on an extension line of the passage of the beam port 23. Both ends of the passage formed by the beam port 23 are closed by the beam windows 26, 27, in order to ensure the sealability of the crucible 21. The beam windows 26, 27 are for instance made up of a metal plate that lets radiation beams through but are not melted by the radiation beams. The interior of the beam port 23 is evacuated or is filled with a gas (for instance He gas). The radiation beam outputted from the radiation beam generator passes through the beam window 26, the interior of the beam port 23 and the beam window 27 and reaches the target substance in the crucible 21.

The gas introduction port 24 is an inlet through which a gas is introduced into the crucible 21. The gas lead-out port 25 is an outlet for discharging a gas from a gas phase portion of the crucible 21. The gas introduction port 24 and the gas lead-out port 25 are for instance tubular pipes. The gas introduction port 24 allows a gas to flow into and out the crucible 21. A gas for recovery of radioisotopes is introduced through the gas introduction port 24. For instance, He gas that is not radioactivated by radiation beams is suitably used as the gas that is introduced into the crucible 21. The gas is introduced through the gas introduction port 24, as a result of which the gas is discharged from the gas lead-out port 25. In consequence, this elicits flow of gas from the gas introduction port 24 towards the gas lead-out port 25, in the gas phase portion in the crucible 21. As a result of such gas flow, it becomes possible to discharge, via the gas lead-out port 25, radioisotopes that are generated in the target substance through irradiation with a radiation beam and that migrate into the gas in the gas phase portion. The flow rate of the gas discharged out of the gas lead-out port 25 and pressure in the crucible 21 can be adjusted by adjusting the flow rate of the gas that is introduced into the crucible 21 through the gas introduction port 24, and/or by adjusting the degree of opening of a flow rate adjustment valve that is provided in the vicinity of the gas lead-out port 25.

Figure 3:
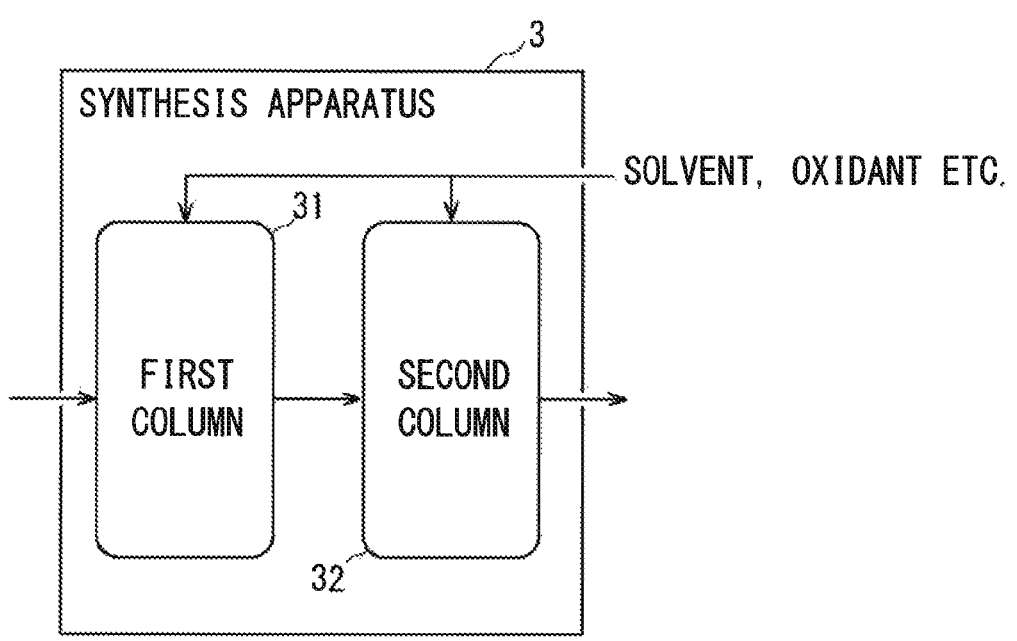
FIG. 3 is a diagram illustrating an example of a synthesis apparatus.

FIG. 3 is a diagram illustrating an example of the synthesis apparatus 3. The synthesis apparatus 3 has two columns for allowing radioisotopes to react with a label precursor, namely a first column 31 through which the gas discharged from the gas lead-out port 25 of the radioisotope producing apparatus 2 passes, and a second column 32 through which gas having passed through the first column 31 passes. The first column 31 selectively captures a first radioisotope from among the two or more radioisotopes generated from the alloy of the target substance in the crucible 21 of the radioisotope producing apparatus 2, to perform an RI labeling reaction of allowing the first radioisotope to react with the label precursor. In the first column 31, therefore, the first radioisotope from among the two or more radioisotopes contained in the gas discharged from the gas lead-out port 25 of the radioisotope producing apparatus 2 is used in an RI labeling reaction, while the second radioisotope passes as-is through the first column 31. At this stage the label precursor having the first radioisotope bound thereto in the first column 31 is one type of intermediate label, as referred to in the present application, since this label precursor precedes binding of the second radioisotope in the second column 32. Specifically, the term intermediate label in the present application denotes a label having bound thereto at least either one of the two or more radioisotopes that are to be bound, at a time prior to completion of binding all of the two or more radioisotopes.

In the second column 32 on the downstream side of the first column 31, the second radioisotope having passed through the first column 31 is captured; the second radioisotope is allowed to react with the intermediate label having been labeled in the first column 31, to generate a final label as a result. Schemes conforming to the compound to be synthesized are utilized in the first column 31 and the second column 32. For instance, a batch method is used in a case where reaction time is long, whereas a flow method is used in a case where reaction time is short.

A normally RI labeling reaction is carried out in the first column 31. In a case for instance where an RI labeling reaction by astatine $^{211}$At is carried out in the first column 31, an electrophilic substitution reaction, a nucleophilic substitution reaction, an electrophilic addition reaction or a radical reaction may be resorted to as a halogenation reaction that can be utilized in the first column 31. In order to bind a radioactive halogen such as astatine $^{211}$At to for instance a peptide, which is a type of carrier, firstly a peptide compound, synthesized on site or procured commercially, is prepared and is bound to a carrier within the first column 31, after which astatine $^{211}$At is bound to the peptide, at an appropriate reaction temperature and during an appropriate reaction time, while under the concomitant use of an appropriate amount of an oxidant and/or a solvent.

The first column 31 is made up of devices conforming to various labeling methods. In an on-column labeling method, for instance, the first column 31 is made up of a solid-phase column that holds a reaction solution, and tubing for allowing the label precursor to pass through the solid-phase column.

In the second column 32 as well an RI labeling reaction is carried out. In the second column 32 the radioisotope having passed through the first column 31 is allowed to react with the intermediate label, having been labeled in the first column 31 and having been transferred from the first column 31 to the second column 32, so that a final label is generated as a result. In a case for instance where astatine $^{211}$At is bound to a peptide in the first column 31, as described above, the peptide having astatine $^{211}$At bound thereto corresponds herein to the intermediate label. Also in the second column 32, a halogenation reaction such as an electrophilic substitution reaction, a nucleophilic substitution reaction, an electrophilic addition reaction or a radical reaction can be utilized, similarly to the first column 31. However, the amount of the intermediate label having been labeled in the first column 31 and supplied to the second column 32 is very small, at most of several tens of pmol; accordingly, a very small space is formed in the second column 32, so as to enable a pico-scale RI labeling reaction to be carried out. The intermediate label generated in the first column 31 is transferred to the second column 32, together with the radioisotope that passes through the first column 31, as a result of unbinding of the intermediate label from the carrier in the first column 31. The method for separating the intermediate label from the carrier in the first column 31 depends on the binding method, but may involve for instance natural separation from the carrier accompanying binding to the radioisotope, or may be a method in which an eluent containing an additive that unbinds the intermediate label from the carrier in the first column 31 is injected. The intermediate label transferred to the second column 32 is bound to a carrier of the second column, within a very small space; the radioisotope having passed through the first column 31 becomes then bound to the intermediate label that is in turn bound to the carrier of the second column. In a case for instance where astatine $^{211}$At and iodine $^{124}$I are fed from the radioisotope producing apparatus 2 to the synthesis apparatus 3 by a gas, as described above, then iodine $^{124}$I having passed through the first column 31 becomes bound to the intermediate label in the second column 32.

Various automation techniques that allow for quick and efficient synthesis are preferably utilized in the synthesis apparatus 3, in order to enable efficient synthesis of a label having a short half-life, such as astatine $^{211}$At, as described above.

Figure 4:
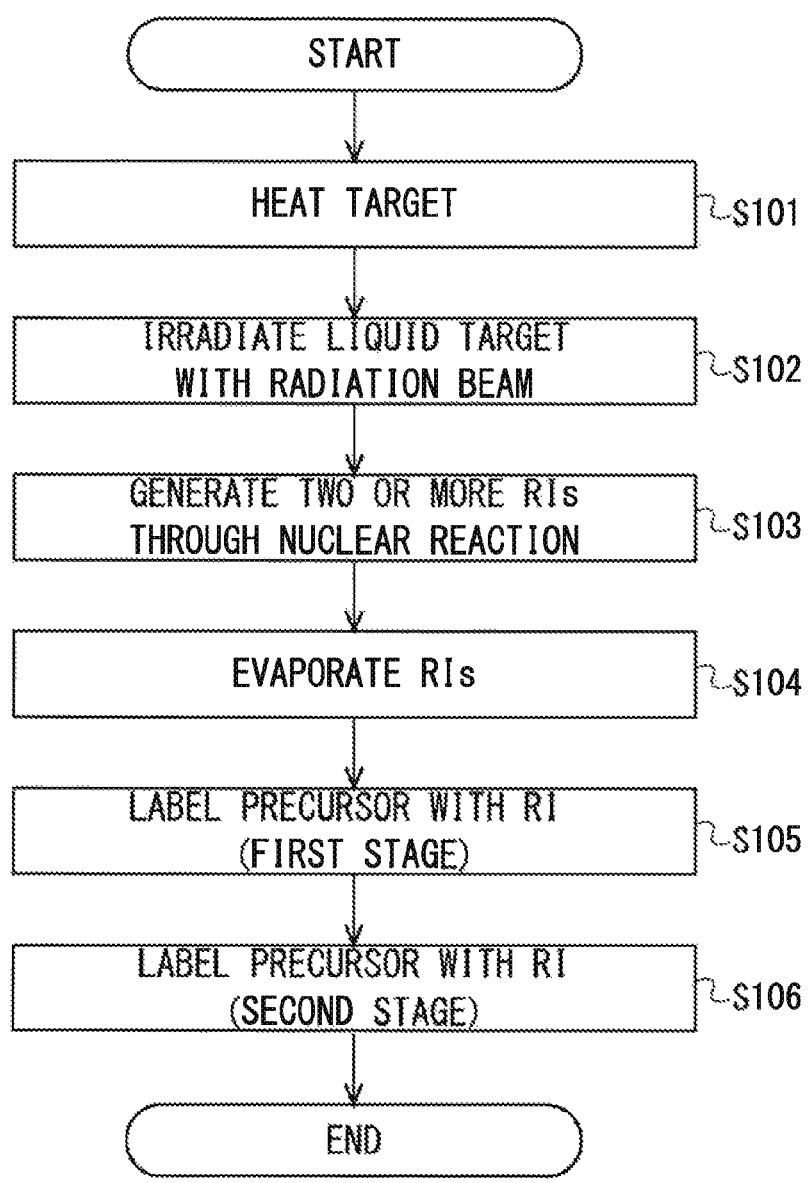
FIG. 4 is an example of a process flow performed in a radiolabeled compound producing apparatus.

FIG. 4 is an example of a process flow performed in the radiolabeled compound producing apparatus 1. Hereafter, the process flow performed in the radiolabeled compound producing apparatus 1 will be explained with reference to the flowchart of FIG. 4.

In the case of generation of a radiolabeled compound using the radiolabeled compound producing apparatus 1, a substance conforming to the label type is placed with the crucible 21 of the radioisotope producing apparatus 2, and a gas is injected through the gas introduction port 24 at an appropriate flow rate. The crucible 21 is heated through energization of the heater 22 (S101). The target substance in the crucible 21 melts when reaching the melting point, and becomes a liquid alloy of the target substance, in the crucible 21. For instance, alloys of bismuth Bi and antimony Sb have a melting point of about 271° C. to 631° C., depending on the alloy ratio; accordingly, the interior of the crucible 21 is preferably brought to a temperature that is at least higher than the melting points of bismuth Bi and antimony Sb, in a case where these are placed in the crucible 21. The alloy ratio is established herein as appropriate taking into consideration for instance the type and structure of the RI drug to be produced, the proportion in which radioactive compounds generated by the radioisotope producing apparatus 2 move into the synthesis apparatus 3, and labeling ratios and reaction times in the first column 31 and the second column 32.

Next, the interior of the crucible 21 is irradiated with a radiation beam via the beam port 23 (S102). Examples of radiation beams that irradiates the interior of the crucible 21 include a-beams ($^{4}He^{2+}$), $^{3}He^{2+}$, $^{1}H^{+}$, $^{2}H^{+}$, $^{7}Li^{3+}$ and the like. The radiation beams utilized are $^{1}H^{+}$, $^{2}H^{+}$, $^{4}He^{2+}$, $^{3}He^{2+}$ or $^{7}Li^{3+}$ in a case where target-constituting substance is an element of group 13, group 14, group 15 or group 16. In consequence, the main radioisotopes generated as a result of a nuclear reaction between the target-constituting substance and the radiation beam are elements of group 15, group 16, group 17 and group 18. In a case where an alloy of bismuth Bi and antimony Sb are stored in the crucible 21, irradiation with a-beams into the crucible 21 results in generation of astatine $^{211}$At and iodine $^{124}$I as radioisotopes, since both bismuth Bi and antimony Sb are group 15 elements.

When the interior of the crucible 21 is irradiated with a radiation beam, at least two radioisotopes become generated in the liquid phase portion of the crucible 21. The multiple radioisotopes generated in the crucible 21 ordinarily have mutually different boiling points. For instance, astatine $^{211}$At has a boiling point of 337° C. at normal pressure (1 atmosphere). The boiling point at normal pressure of iodine $^{124}$I is however 184° C. In the radiolabeled compound producing apparatus 1 a configuration is adopted wherein the multiple radioisotopes generated in the crucible 21 and having migrated from the liquid phase portion into the gas in the gas phase portion are fed to the synthesis apparatus 3; accordingly, the multiple radioisotopes generated in the crucible 21 must all evaporate in the crucible 21 and migrate from the liquid phase portion into the gas in the gas phase portion. In the radiolabeled compound producing apparatus 1 of the present embodiment, therefore, the temperature in the interior of the crucible 21 is adjusted, for instance by the heater 22, so as to be higher than the boiling point of at least the radioisotope of highest boiling point from among the multiple radioisotopes that are to be fed to the synthesis apparatus 3. The temperature in the interior of the 21 is adjusted for instance to be 337° C. or higher, although depending on the pressure in the crucible 21, in a case for instance where both astatine $^{211}$At and iodine $^{124}$I are allowed to evaporate in the crucible 21 and migrate from the liquid phase portion into the gas in the gas phase portion. The boiling point of bismuth Bi is 1564° C. and the boiling point of antimony Sb is 1587° C. The boiling point of alloys of bismuth Bi and antimony Sb is about 1562° C. to 1650° C., depending on the alloy ratio; accordingly, a liquid alloy which is the target substance does not evaporate so long as the interior of the crucible 21 is kept at a temperature lower than that.

The radioisotopes that evaporate from in the crucible 21 and move from the liquid phase portion in the crucible 21 into the gas in the gas phase portion flow out of the crucible 21, and into the synthesis apparatus 3, together with He gas that flows from the gas introduction port 24, through the interior of the crucible 21, and towards the gas lead-out port 25. In the first column 31 of the synthesis apparatus 3 the first radioisotope, from among the two or more radioisotopes contained in the He gas that flows from the radioisotope producing apparatus 2 towards the synthesis apparatus 3, becomes bound to a label precursor, to generate an intermediate label. In the second column 32 of the synthesis apparatus 3, the second radioisotope having passed through the first column 31, from among the two or more radioisotopes contained in the He gas that flows from the radioisotope producing apparatus 2 towards the synthesis apparatus 3, becomes bound to the intermediate label, and a final label is generated thereupon.

In a case for instance where an alloy of bismuth Bi and antimony Sb is stored as a target substance in the crucible 21, and astatine $^{211}$At and iodine $^{124}$I generated in the crucible 21 as a result of irradiation with a-beams flow from the radioisotope producing apparatus 2 into the synthesis apparatus 3, then an intermediate label in which astatine $^{211}$At is bound to a label precursor is generated in the first column 31, and a final label, in which iodine $^{124}$I is further bound to the intermediate label, is generated in the second column 32.

In the radiolabeled compound producing apparatus 1 of the embodiments, thus, an alloy serves as the target substance, and accordingly two or more types of objective radioisotopes can be generated simultaneously within a liquid target, and a radiolabeled compound that is labeled with two or more radioisotopes can likewise be generated, through irradiation of the alloy as the target substance with a same radiation beam. The radiolabeled compound thus labeled with two or more radioisotopes can be used for instance in the manner described below.

Figure 5:
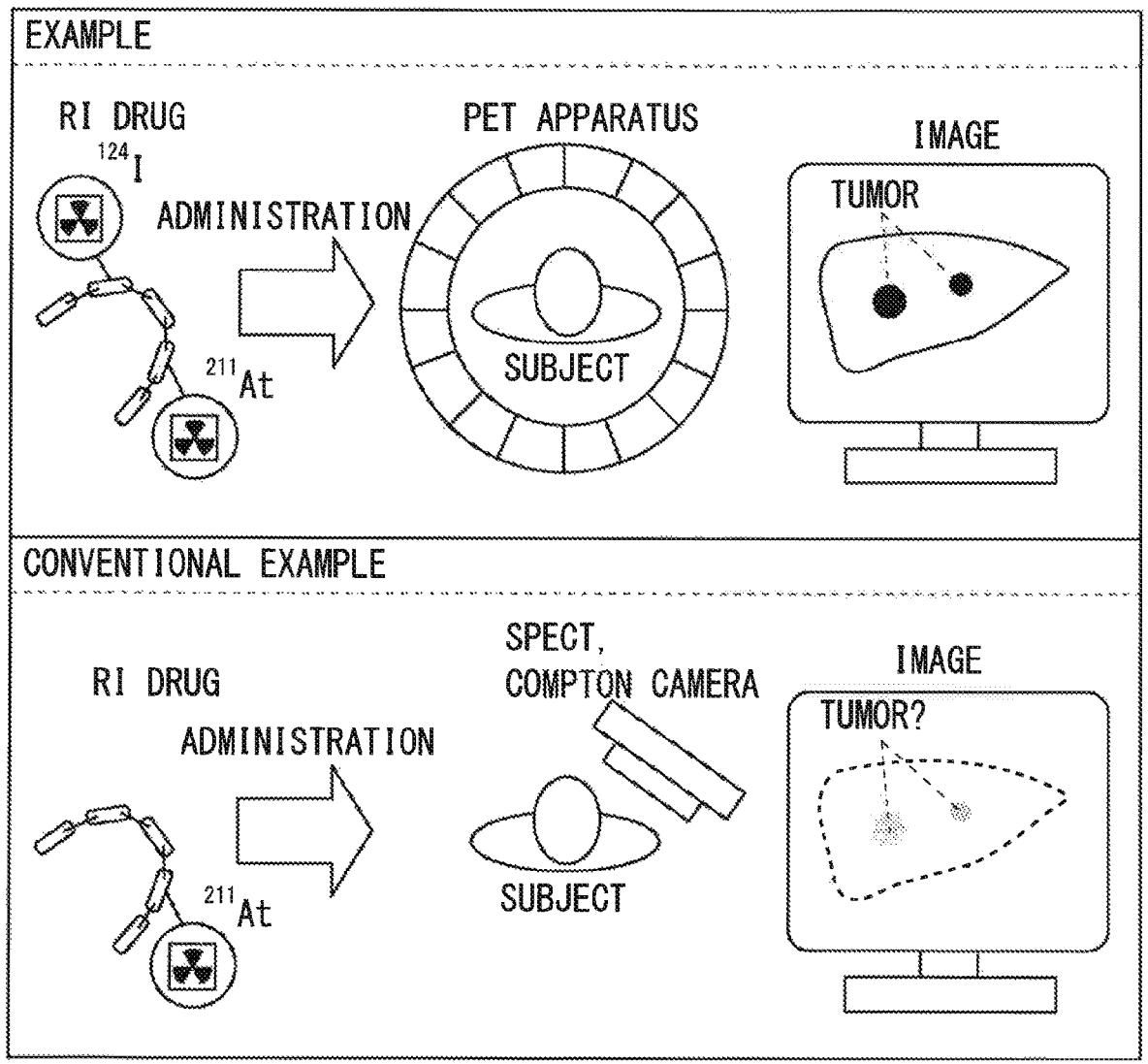
FIG. 5 is an image diagram illustrating cancer treatment and diagnosis.

FIG. 5 is an image diagram illustrating cancer treatment and diagnosis. For instance, astatine $^{211}$At having received attention in recent years as an a ray emitting nuclide for cancer treatment emits herein a-ray capable of selectively destroying cancer cells alone, since the range of astatine $^{211}$At within the body is short. However, images of an RI drug taken up by cancer cells are indistinct, and insufficient for clinical use, as depicted by the "image" in the comparative example section of FIG. 5, due for instance to sensitivity and resolution problems that arise when attempting to capture human biodistribution of an RI drug labeled with astatine Hi which has a short half-life of about 7.2 hours, by single photon emission computed tomography (SPECT) or using a Compton camera, both techniques being sensitive to X-rays and gamma rays radiated by astatine $^{211}$At. By contrast, iodine $^{124}$I has a comparatively long half-life of about 4.2 days, and accordingly the human biodistribution of an RI drug labeled with iodine $^{124}$I can be captured by a positron emission tomographic (PET) apparatus for positron emission tomography, which is an imaging technique relying on positron detection; as depicted by the "image" in the working example section of FIG. 5; an image of an RI drug taken up by cancer cells is clearly reflected in this case, and can be sufficiently used in a clinical setting.

For instance as reported by D. Scott Wilbur et al. in NPL 3 above, the biodistribution of the RI drug having astatine $^{211}$At bound thereto are not identical to the biodistribution of an RI drug having iodine $^{124}$I bound thereto, even for a same label precursor. In conventional art it is therefore necessary to address differences in the distribution of both drugs where laying out a cancer treatment plan. In this regard, the radiolabeled compound producing apparatus 1 of the above embodiment allows two radioisotopes, namely astatine $^{211}$At and iodine $^{124}$I, to be bound to a single carrier, and accordingly allows finely imaging, by means of a PET apparatus, the distribution of an RI drug administered for the purpose of treating cancer. Herein a radiolabeled compound that may be grasped under the appellation of "chimera RI drug" can be used as an RI drug that fulfills two functions, namely a therapeutic function and an imaging function, through binding of two radioisotopes, i.e. astatine $^{211}$At and iodine $^{124}$I having different natures, to a single carrier, despite the fact the radiolabeled compound is labeled with astatine $^{211}$At having a comparatively short half-life. The feasibility of using such a chimera RI drug derives from the fact that the radiolabeled compound is produced using the radiolabeled compound producing apparatus 1 of the above embodiment, which allows generating simultaneously two or more radioisotopes through irradiation of an alloy as a target substance with a radiation beam, and allows binding the two or more radioisotopes to a label precursor in a short time. Such a chimera RI drug cannot be produced, on account of time constraints, in conventional producing methods that involve, for instance, irradiating a solid target with a radiation beam, and extracting a radioisotope, generated within the solid target, for instance by dry distillation.

In the configuration of the radiolabeled compound producing apparatus 1 of the above embodiment, the first column 31 and the second column 32 of the synthesis apparatus 3 are disposed in series, such that the gas discharged from the gas lead-out port 25 of the radioisotope producing apparatus 2 follows a path leading through the first column 31, after which the gas flows to the second column 32. However, the first column 31 and the second column 32 in the radiolabeled compound producing apparatus 1 may be disposed in parallel.

Figure 6:
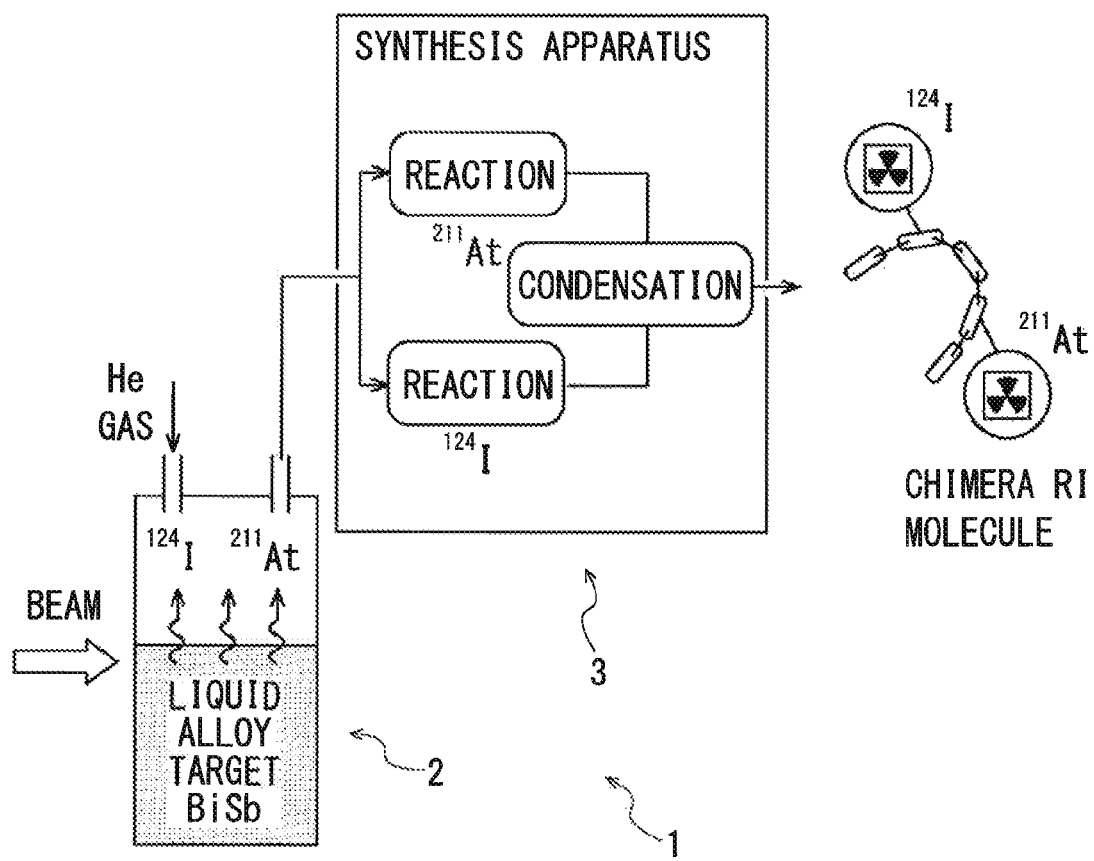
FIG. 6 is a diagram illustrating a first variation of a radiolabeled compound producing apparatus.

FIG. 6 is a diagram illustrating a first variation of the radiolabeled compound producing apparatus 1. In the radiolabeled compound producing apparatus 1 of the above embodiment, a configuration may be adopted wherein the columns in which the radioisotopes become bound to the label precursor are provided as two columns in parallel, such that the gas discharged from the gas lead-out port 25 of the radioisotope producing apparatus 2 flows in parallel in the two columns, as illustrated in FIG. 6. In that case two or more radioisotopes generated from the alloy of a target substance in the crucible 21 of the radioisotope producing apparatus 2 flows in the two columns in the synthesis apparatus 3. Therefore, in one of the two columns of the synthesis apparatus 3 in the case of the present first variation an RI labeling reaction is carried out in which a first radioisotope, from among the two or more radioisotopes generated from the alloy of the target substance in the crucible 21 of the radioisotope producing apparatus 2, is selectively captured, and is allowed to react with a label precursor, to generate a first intermediate label. In the other of the two columns of the synthesis apparatus 3 an RI labeling reaction is carried out in which a second radioisotope different from the first radioisotope, from among the two or more radioisotopes generated from the alloy of the type the target substance in the crucible 21 of the radioisotope producing apparatus 2 is selectively captured, and is allowed to react with the label precursor, to generate a second intermediate label. The first intermediate label and the second intermediate label generated in the respective columns are then condensed, to generate a final label.

In a case for instance where an RI drug of astatine $^{211}$At and iodine $^{124}$I such as the one exemplified in the above embodiment is produced in accordance with the present first variation, an RI labeling reaction of allowing astatine $^{211}$At to react with a label precursor is performed in one of the two columns of the synthesis apparatus 3. An RI labeling reaction of allowing iodine $^{124}$I to react with a label precursor is carried out in the other of the two columns of the synthesis apparatus 3. For instance, any one from among an electrophilic substitution reaction, a nucleophilic substitution reaction, an electrophilic addition reaction and a radical reaction can be resorted to in the column where astatine $^{211}$At is allowed to react with the label precursor, but an electrophilic substitution reaction is most suitable herein. Meanwhile, for instance any one from among an electrophilic substitution reaction, a nucleophilic substitution reaction, an electrophilic addition reaction, a nucleophilic addition reaction and a radical reaction may be resorted to in the column in which iodine $^{124}$I is allowed to react with a label precursor; preferred herein are however an electrophilic substitution reaction, a nucleophilic substitution reaction and an electrophilic addition reaction, and a radical reaction as a next preferred reaction.

The intermediate label of astatine $^{211}$At and the intermediate label of iodine $^{124}$I respectively generated in the two columns of the synthesis apparatus 3 are debound from the carrier in each column, are retrieved, and are condensed in another column. In the column in which condensation is carried out, a very small space for pico-scale condensation is formed, similarly to the above-described second column 32, since the intermediate labels are condensed with each other in the pico-scale. Upon condensation of the intermediate label of astatine $^{211}$At and the intermediate label of iodine $^{124}$I a final label becomes perfected in the form of a chimera RI drug in which two radioisotopes, namely astatine $^{211}$At and iodine $^{124}$I are bound to a single carrier.

In the present first variation as well, similarly to the above embodiment, two or more radioisotopes can be generated simultaneously within a liquid target, and a radiolabeled compound that is labeled with the two or more radioisotopes can be generated, through irradiation of an alloy as the target substance with a radiation beam. Thus, a radiolabeled compound having been thus labeled with two or more radioisotopes can be used as an RI drug that delivers both a therapeutic function and an imaging function, as described above.

In the above embodiment an implementation is adopted in which the radioisotopes generated in the liquid phase portion of the crucible 21 flow into the synthesis apparatus 3 from the gas phase portion of the crucible 21, but the radiolabeled compound producing apparatus 1 of the above embodiment is not limited to such a configuration.

Figure 7:
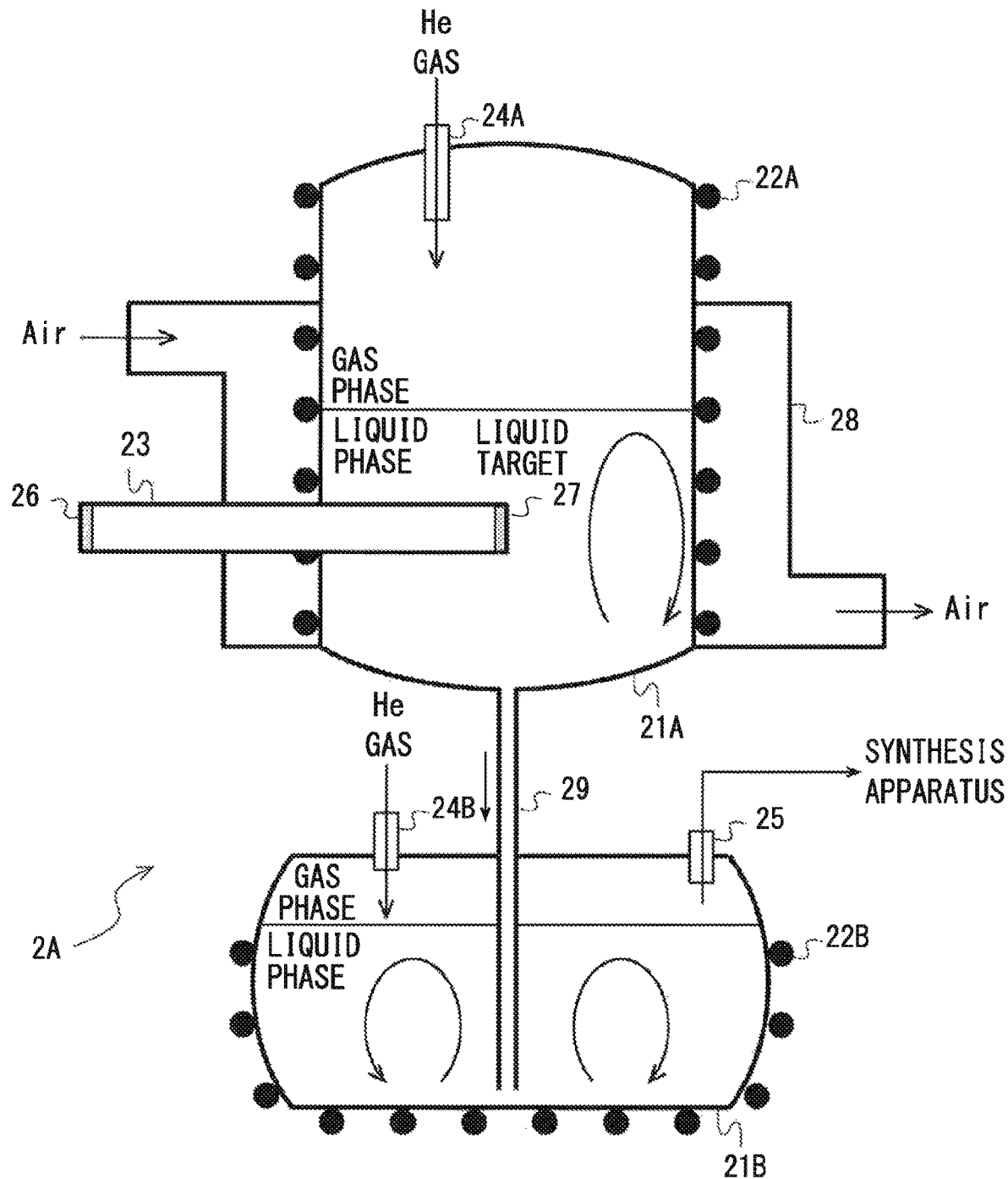
FIG. 7 is a diagram illustrating a variation of a radioisotope producing apparatus.

FIG. 7 is a diagram illustrating a variation of a radioisotope producing apparatus. In the present modification, constituent elements identical to those in the above embodiment are denoted by the same reference numerals, and a detailed description thereof will be omitted. A radioisotope producing apparatus 2A according to the present variation has a configuration wherein the crucible 21 according to the above embodiment is herein separated into a target container 21A and a storage container 21B. Similarly to the crucible 21 according to the above embodiment, the target container 21A is provided with a heater 22A that heats up an alloy within the target container 21A, a beam port 23 for irradiating an alloy within the target container 21A with a radiation beam, and a gas introduction port 24A for introducing a gas into the crucible 21. Beam windows 26, 27 are provided in the beam port 23. A jacket 28 is provided in the target container 21A.

The target container 21A is a container for storing, in the interior thereof, a target-constituting substance, and for melting at least part of the target substance. Similarly to the crucible 21, the target container 21A is heat-resistant so as to be capable of withstanding the temperature of the melting point of target-constituting substance. A transfer pipe 29 for transfer of a liquid alloy from the interior of the target container 21A towards the storage container 21B is connected to the bottom of the target container 21A.

The storage container 21B is a storage container that receives the liquid alloy transferred from the target container 21A. Similarly to the target container 21A, the storage container 21B has heat resistance that allows withstanding the temperature of the melting point of the liquid alloy transferred from the target container 21A. An opening at the end of a transfer pipe 29 is disposed in the vicinity of the bottom of the storage container 21B, so that the liquid alloy flowing through the transfer pipe 29 flows out into the storage container 21B at the liquid phase portion of the storage container 21B. The storage container 21B is provided with a heater 22B for heating the alloy within the storage container 21B, a gas introduction port 24B for feeding a gas into the gas phase portion of the storage container 21B, and a gas lead-out port 25 for feeding gas from the gas phase portion of the storage container 21B to the synthesis apparatus 3. The storage container 21B also functions as a heating container for heating the liquid alloy transferred from the target container 21A.

The explanation in FIG. 7 deals with an example of a configuration wherein the gas lead-out port 25 that is connected to the synthesis apparatus 3 is not provided in the target container 21A, but this implementation is not limiting. A gas lead-out port 25 connected to the synthesis apparatus 3 may be provided in the target container 21A.

The heater 22A and the heater 22B in the radioisotope producing apparatus 2A according to the present variation can be controlled as follows. As described above, the boiling point of for instance astatine $^{211}$At at normal pressure (1 atmosphere) is 337° C., and the boiling point of iodine $^{124}$I at normal pressure is 184° C.; hence, it was necessary to adjust the temperature in the interior of the crucible 21 for instance to be 337° C. or higher, in order to allow both astatine $^{211}$At and iodine $^{124}$I to evaporate in the radioisotope producing apparatus 2 of the above embodiment, and allow astatine $^{211}$At and iodine $^{124}$I to migrate from the liquid phase portion into the gas in the gas phase portion. In the radioisotope producing apparatus 2A according to the present variation, however, a configuration is adopted in which the liquid alloy in the target container 21A is transferred to the storage container 21B, and accordingly astatine $^{211}$At and iodine $^{124}$I can be allowed to evaporate within the storage container 21B, and allowed to migrate from the liquid phase portion into the gas in the gas phase portion, by bringing the storage container 21B to 337° C. or above by means of the heater 22B. That is, the temperature in the target container 21A can be adjusted to a temperature lower than 337° C. In a case where the beam windows 26, 27 cannot withstand a temperature of 337° C. or higher, the present variation allows therefore astatine $^{211}$At and iodine $^{124}$I to migrate into the gas in the gas phase portion, even if the target container 21A is brought to the heat resistance temperature of the beam windows 26, 27.

Figure 8:
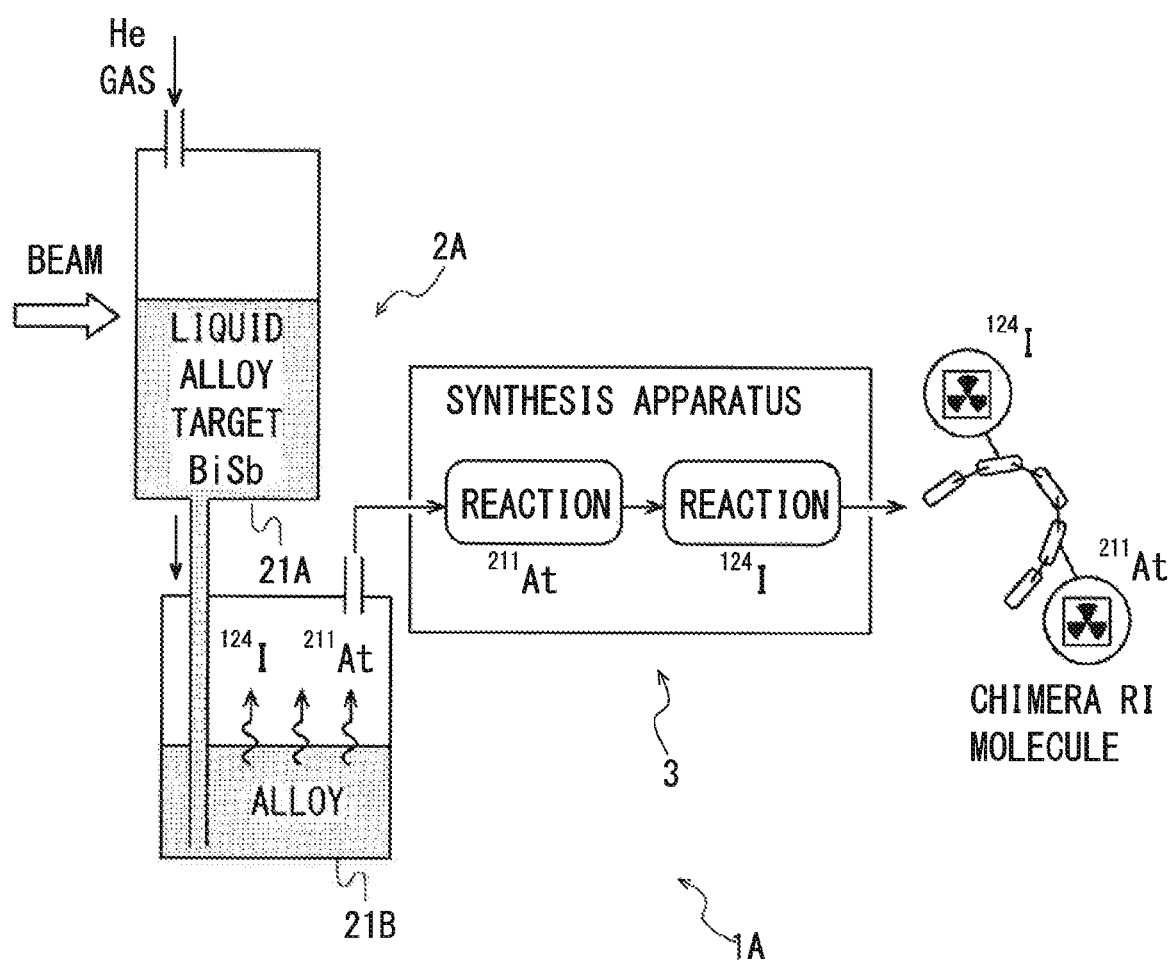
FIG. 8 is a diagram illustrating a second variation of a radiolabeled compound producing apparatus.

FIG. 8 is a diagram illustrating a second variation of the radioisotope producing apparatus. In a radiolabeled compound producing apparatus 1A according to the present second variation, an alloy as a target substance within the target container 21A is irradiated with a radiation beam, to generate two or more radioisotopes in the alloy, whereupon the alloy that has given rise to the radioisotopes is transferred to the storage container 21B, the radioisotopes migrate into a gas in the storage container 21B, and the radioisotopes are combined with a label precursor in the synthesis apparatus 3.

Also in the radiolabeled compound producing apparatus 1A of the present second variation, an alloy serves as the target substance, as in the radiolabeled compound producing apparatus 1 of the above embodiment. Accordingly, two or more types of objective radioisotopes can be generated simultaneously within a liquid target, and a radiolabeled compound that is labeled with two or more types of radioisotopes can be generated, through irradiation of the alloy as the target substance with a same radiation beam.

In the above embodiment and the first and second variations, examples of a radiolabeled compound have been illustrated in the form of an RI drug labeled with astatine $^{211}$At and iodine $^{124}$I, through irradiation of an alloy of bismuth Bi and antimony Sb with a radiation beam. However, the above embodiment and variations are not limited to such an implementation. The radiolabeled compound produced in the radiolabeled compound producing apparatus 1 may result from incorporating for instance sulfur S, gallium Ga, selenium Se, tin Sn, tellurium Te, lead Pb or the like into a target substance, to thereby generate various radioisotopes of chlorine Cl, arsenic As, bromine Br or the like that are then bound to a single carrier.

Second Embodiment

The radioisotope producing apparatus 2A in the above variation can be used for instance by being replaced by a crucible according to the embodiment described below.

Figure 9:
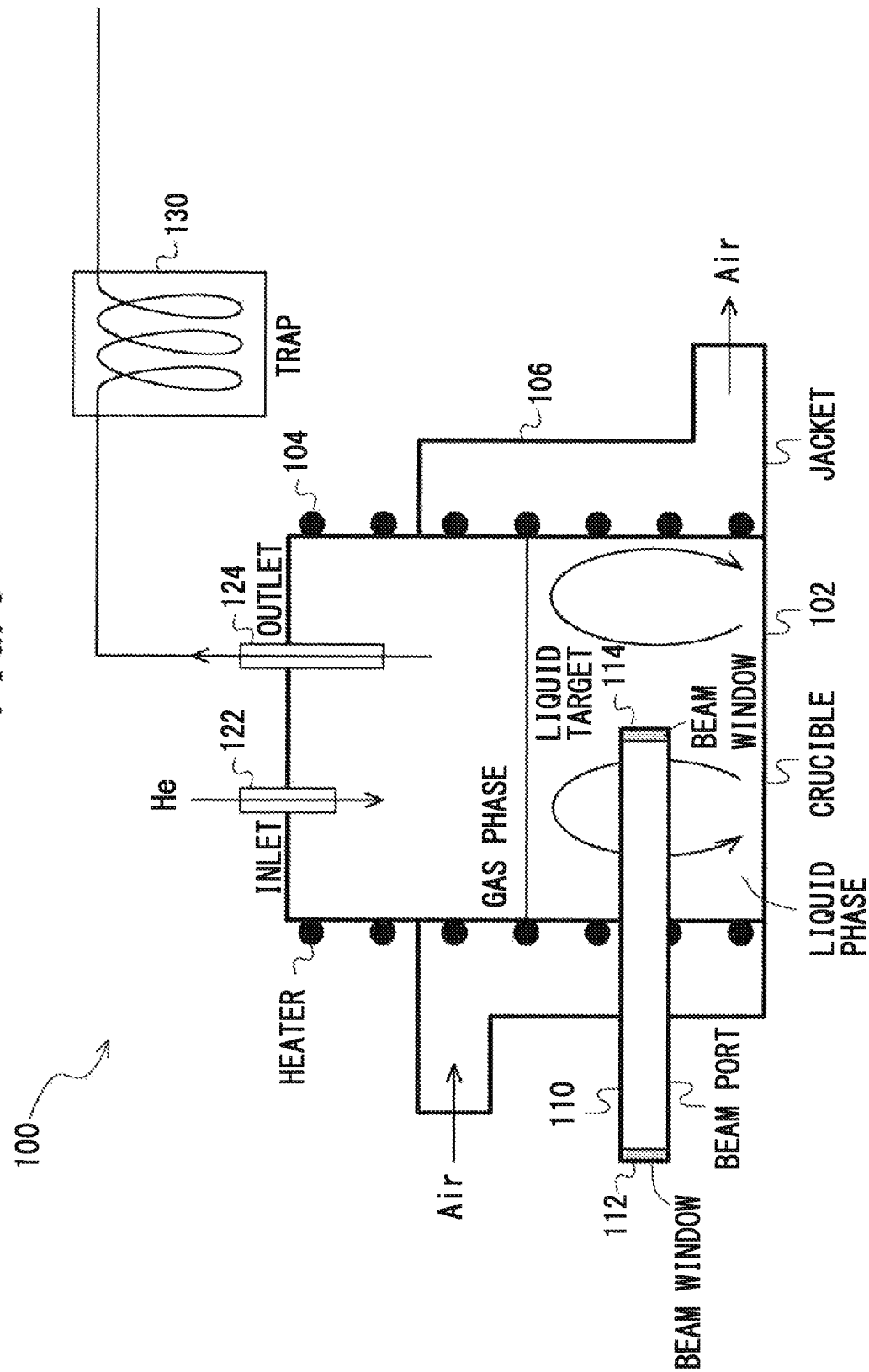
FIG. 9 is a diagram illustrating a configuration example of a radioisotope producing apparatus of a second embodiment.

FIG. 9 is a diagram illustrating a configuration example of a radioisotope producing apparatus of the present second embodiment. A radioisotope producing apparatus 100 has a crucible 102, a heater 104, a jacket 106, a beam port 110, a beam window 112, a beam window 114, an inlet 122, an outlet 124 and a trap 130.

The crucible 102 is a heat-resistant container in which a substance that constitutes a target (for instance bismuth) is melted. The crucible 102 is a storage container that stores a target-constituting substance. For instance, quartz, a ceramic or a metal is used as the crucible 102. The crucible 102 is required to be at least heat-resistant enough to withstand a temperature of the melting point of the target-constituting substance. The crucible 102 is sealed, but a gas can be led into and out of the crucible 102 via the inlet 122 and the outlet 124. A beam port 110 is connected to the crucible 102. The crucible 102 is an example of a heat-resistant container.

The heater 104 is a heating means for heating the crucible 102. The heater 104 heats the crucible 102 up, to thereby heat up the target-constituting substance in the crucible 102. This allows promoting melting of the target substance. The target substance is typically melted and liquefied. For instance, a micro sheath heater is used as the heater 104. The heater 104 is not limited to a micro sheath heater. Further, the target-constituting substance in the crucible 102 need not liquefy entirely. That is, part of the target-constituting substance may remain as a solid. The target-constituting substance liquefies when heated by the heater 104. In the interior of the crucible 102, there is a liquid phase by the liquefied substance, and a gas phase from a gas or the like that is introduced from the inlet 122. The heater 104 is an example of a heating unit.

Herein an instance is exemplified in which a target substance is heated by the heater 104, and the substance is liquefied, but the heating means is not limited thereto. For instance, the rise in temperature that is elicited in a beam irradiation portion upon irradiation of the target substance with a radiation beam (rise in temperature derived from heat from a nuclear reaction) can also be exploited herein. A combination of two or more conventionally known heating means can also be used, for instance heating by the heater 104, and warming derived from irradiation with the radiation beam.

The jacket 106 is a cooling space disposed around the crucible 102. An inlet and an outlet for a coolant (for instance air) are provided in the jacket 106, such that the crucible 102 is cooled through introduction of the coolant into the jacket 106 via the inlet. Cooling can be accomplished by discontinuing heating by the heater 104, or more quickly through introduction of the coolant into the jacket 106. The coolant introduced into the jacket 106 is not limited to air (for instance air at normal temperature), and may be another gas such as nitrogen, or a liquid such as water.

And instance where the crucible 102 is cooled through introduction of a coolant into the jacket 106 is explained herein as an example of a cooling method of the crucible 102, but the cooling method is not limited thereto, and a combination of one, two or more conventionally known cooling means can be resorted to. For instance, an element such as a Peltier element can be used herein.

The beam port 110 is a passage for introduction of the radiation beam that irradiates the target-constituting substance in the crucible 102. The interior of the beam port 110 is evacuated or has a gas (for instance He gas) introduced thereinto. The beam port 110 has a tubular shape both ends of which are plugged by the beam window 112 and the beam window 114. The beam window 112 is connected to a radiation beam generator such as an accelerator. The beam window 112 and the beam window 114 are, for instance, metal plates. A radiation beam accelerated by an accelerator or the like included in the radiation beam generator enters the beam port 110 from the beam window 112, passes through the beam window 114, and strikes into the crucible 102. The target (typically a liquefied liquid target) is irradiated in this manner. The beam window 112 and the beam window 114 are substances through which at least part of the radiation beam can pass. The beam window 114 is a substance that does not melt even at the temperature of the liquid target in the interior of the crucible 102. The beam port 110, the beam window 112 and the beam window 114 are examples of beam introduction portions.

The inlet 122 is an inlet through which a gas is introduced into the crucible 102. The inlet 122 is for instance a tubular pipe. The inlet 122 connects the interior and the exterior of the crucible 102, so that a gas can be led into/out of the crucible 102. A gas for recovery of radioisotopes is introduced through the inlet 122. The gas which can be preferably used includes a gas that does not liquefy or solidify through cooling by the below-described trap 130. The above gas is for instance He gas. The gas is introduced through the inlet 122 and is discharged as a result from the outlet 124. In consequence, this elicits flow of gas from the inlet 122 towards the outlet 124, in the gas phase in the crucible 102. As a result of such gas flow it becomes possible to convey, towards the outlet, the radioisotopes having migrated into the gas phase. The amount of gas discharged from the outlet 124 can be adjusted through adjustment of the amount of gas introduced through the inlet 122. The pressure of the gas phase in the crucible 102 can be controlled for instance through adjustment of the amount of gas that is introduced, for example by adjusting the amount of gas that is discharged from the outlet 124 (for instance by reducing the flow rate of the gate, and typically plugging the outlet 124), or by plugging the discharge side of the trap 130. The pressure of the gas phase in the crucible 102 can be controlled, with yet higher precision, by combining adjustment of the amount of gas discharged from the outlet 124 or adjustment of the amount of gas discharged from the discharge side of the trap 130, with adjustment of amount of gas that is introduced through the inlet 122.

The outlet 124 is an outlet through which gas from the crucible 102 is discharged. The outlet 124 is, for instance, a tubular pipe. The outlet 124 connects the interior of the crucible 102 and the trap 130, so that a gas can be led out of the crucible 102 and into the trap 130. For instance, the gas introduced through the inlet 122, and vaporized radioisotopes, are discharged from the outlet 124. The radioisotopes are substances generated through irradiation of a liquid target with a radiation beam.

The trap 130 is a device for separating and extracting the radioisotope from the gas introduced from the crucible 102. The trap 130 is hermetically connected to the crucible 102, so as to enable conveyance of a gas containing the radioisotopes. For instance, the gas introduced from the crucible 102 is cooled in the trap 130. As a result, it becomes possible to separate radioisotopes from the gas (typically a mixed gas with He) that contains the radioisotopes, through liquefaction or solidification of the radioisotopes. The cooling is not particularly limited as long as the radioisotopes can be separated from the gas mixture; for instance, the cooling temperature may be set to or lower than the boiling points of the radioisotopes, and preferably equal to or lower than the melting points or equal to or lower than the freezing points of the radioisotopes. More preferably, the cooling temperature is set to be lower than the melting points and the freezing points of the radioisotopes. For instance, the cooling temperature can be set to be 4° C. (277K) or lower, typically −10° C. (263K) or lower, preferably −80° C. (193K) or lower, and more preferably −196° C. (77K) or lower. For instance, cooling water, acetone-dry ice, liquid nitrogen or the like can be used as a cooling means. The radioisotopes can be separated herein since He gas does not liquefy or solidify at the temperature of liquid nitrogen (77K). The separated gas (for instance He gas), discharged from the trap 130, may be introduced again through the inlet 122 into the crucible 102. In the trap 130 the radioisotopes can be separated in accordance with a method similar to conventionally known dry distillation. The trap 130 is an example of an extraction unit.

A temperature measuring means such as one or more thermocouples may be disposed in the crucible 102. The temperature measuring means allows measuring the temperature at a position of the liquid phase and the temperature at the position of the gas phase, in the crucible 102. It is for instance possible to determine whether the target-constituting substance is liquefied or not, through measurement of the temperature of the liquid phase position.

Operation Example

Figure 10:
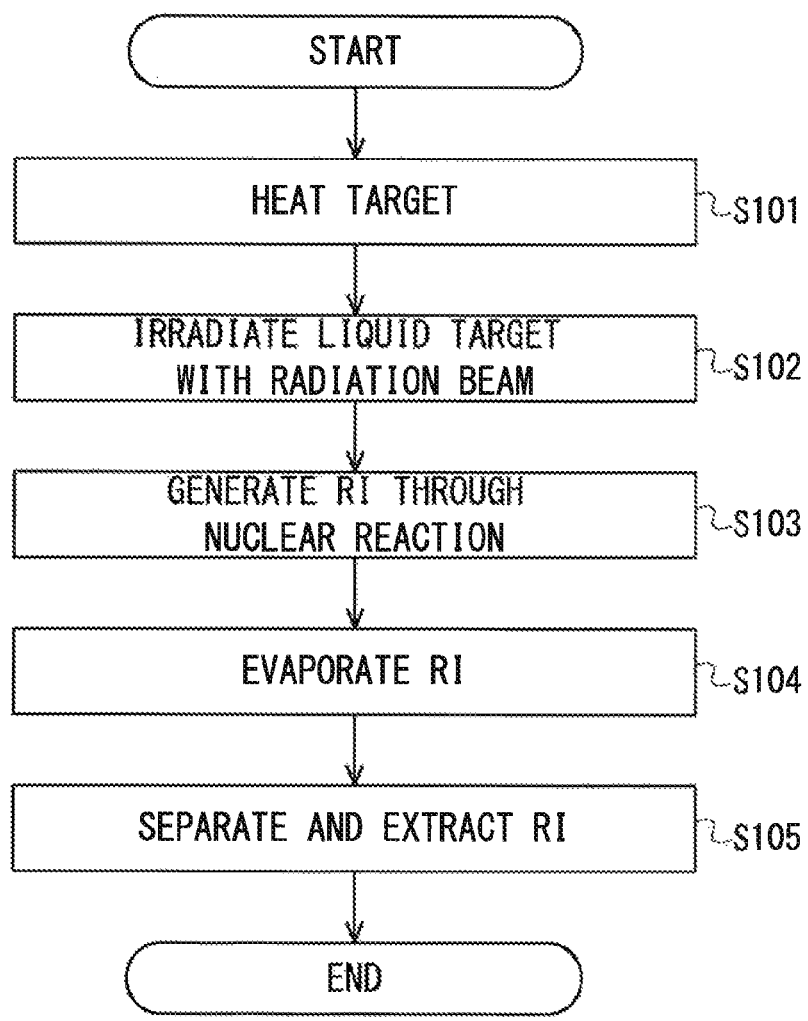
FIG. 10 is a diagram illustrating an example of the operation flow of a radioisotope producing apparatus.

FIG. 10 is a diagram illustrating an example of the operation flow of the radioisotope producing apparatus. Herein a target-constituting substance is already disposed in the crucible 102. A predetermined amount of He gas per unit time is introduced through the inlet 122.

In S101, the heater 104 of the radioisotope producing apparatus 100 heats up the crucible 102. The heater 104 may be controlled for instance by a control device, for instance by a computer or the like. The target-constituting substance in the crucible 102 is heated (typically, melted to a liquid) as a result of heating of the crucible 102. Preferably, the crucible 102 is heated to a temperature at or above the melting point of the target-constituting substance. The target-constituting substance having become a liquid will also be referred to as liquid target. Herein bismuth (Bi) serves as the target-constituting substance. The target-constituting substance is for instance an element of group 14, group 15 or group 16 of the periodic table. The melting point of bismuth is 271° C., and accordingly it suffices to heat up the crucible 102 at a temperature of 271° C. or higher. Herein the crucible 102 is set to be heated to 300° C. by the heater 104. The temperature of the target (liquid target) is preferably a temperature at which the proportion of the saturated vapor pressure of the respective generated radioisotope, relative to the saturated vapor pressure of the liquid target, is high. In order to efficiently obtain an objective radioisotope, it is preferable to select a respective target element such that the proportion of the saturated vapor pressure of the generated radioisotope relative to the saturated vapor pressure of the liquid target is high. The type of the radiation beam to be projected in this case is selected as described further on.

In S102, the liquid target in the crucible 102 is irradiated with a radiation beam, via the beam port 110. Examples of radiating of the radiation beam include for instance a-beams ($^{4}He^{2+}$), $^{3}He^{2+}$, $^{1}H^{+}$, $^{2}H^{+}$, $^{7}Li^{3+}$ and the like. Herein a-beams serve as the radiating of the radiation beam. The radiation beams utilized are $^{1}H^{+}$, $^{2}H^{+}$, $^{4}He^{2+}$, $^{3}He^{2+}$ or $^{7}Li^{3+}$ in a case where target-constituting substance is an element of group 13, group 14, group 15 or group 16. In consequence, the main radioisotopes generated as a result of a nuclear reaction between the target-constituting substance and the radiation beam are elements of group 15, group 16, group 17 and group 18. Preferably, the element of the target is a metal.

In S103, a radioisotope is generated as a result of a nuclear reaction between the target-constituting substance and the radiation beam. The target-constituting substance is Bi, and the main radioisotope that is generated is $^{211}At$, when the radiation beam is □-beams. Within the liquid phase of the crucible 102, moreover, Bi warmed by the heat of the nuclear reaction rises up, whereas Bi cooled by the gas in the gas phase, or air or the like passing through the wall of the crucible 102, descends; convection of Bi is driven thereby. The temperature of Bi in the liquid phase can be kept constant thereby.

In S104, the radioisotope generated through irradiating with the radiation beam evaporates. For instance, the saturated vapor pressure of At, at the melting point (302° C.), is $4 \times 10^{4}$ Pa. The generated At evaporates until the partial pressure of At in the crucible 102 reaches the saturated vapor pressure. For instance, the saturated vapor pressure of Bi at the melting point (271° C.) is $1.6 \times 10^{-5}$ Pa. The generated Bi evaporates until the partial pressure of Bi in the crucible 102 reaches the saturated vapor pressure. Assuming that the saturated vapor pressure of At, at the melting point of Bi (271° C.), is substantially the same as the saturated vapor pressure at the melting point of At (302° C.), then the saturated vapor pressure of At is $10^9$ times or more larger than the saturated vapor pressure of Bi. In the liquid phase of the crucible 102, therefore, most of the elements that evaporate from the liquid surface (elements migrating from the liquid phase to the gas phase) is At, since the partial pressure of Bi reaches immediately the saturated vapor pressure in the gas phase, even if the proportion of At with respect to Bi is very small. In a case for instance where the temperature of the liquid target is 300° C., the proportion of At in the elements evaporated from the liquid surface is 99% or higher, if the volume of Bi is appropriately set. That is, At constitutes most of the elements that evaporate from the liquid surface. The amount of At present in the gas phase is much larger than the amount of Bi present in the gas phase. Thus, At becomes separated from Bi as a result.

In a case where the saturated vapor pressure of an element generated by irradiation is high relative to the saturated vapor pressure of the target-constituting element, the greater part of the element evaporated from the liquid surface of the liquid phase is the element (radioisotope) to be generated. The radioisotope migrates into the generated gas phase (into the gas) as a result of irradiation of the target-constituting element with a radiation beam.

FIG. 11 is a table illustrating examples of the relationship between the saturated vapor pressure of elements in group 14, group 15, group 16 and group 17, and temperature. For instance, the saturated vapor pressure of Ge in group 14, at 2014° C., is $10^3$ Pa. It is known that in principle the saturated vapor pressure of an element increases monotonically with temperature. The saturated vapor pressures of elements of a same period are compared herein. In the table of FIG. 11, a comparison between identical saturated vapor pressures reveals that the temperatures in the elements of group 14, group 15 and group 16 are higher than the temperatures in group 17. In a comparison at a same temperature, the saturated vapor pressures of elements of group 14, group 15 and group 16 are lower than the saturated vapor pressures of elements of group 17. Generally, the boiling points of elements of group 18 are very much lower than the boiling points of other elements. In a comparison at a same temperature, therefore, the saturated vapor pressures of elements of group 14, group 15 and group 16 are lower than the saturated vapor pressures of elements of group 18. That is, the saturated vapor pressures of the elements of group 14, group 15 and group 16, at the melting points of the elements of group 14, group 15 and group 16, are lower than the saturated vapor pressures of the elements of group 17 and group 18 at the melting points of the elements of group 14, group 15 and group 16. In other words, the elements of group 17 and group 18 are gaseous at the melting points of the elements of group 14, group 15 and group 16. The proportion of radioisotope with respect to the element evaporated from the liquid surface rises through the use of an element of group 14, group 15 or group 16 as the liquid target, and by setting an element of group 17 or group 18 as the element (radioisotope) to be generated.

In S105 the radioisotope (for instance $^{211}$At) evaporated from the liquid surface of the liquid phase into the gas phase passes through the outlet 124 together with for instance He gas of the gas phase and reaches the trap 130. The radioisotope is extracted in the trap 130 for instance through cooling using liquid nitrogen or the like. At the time of cooling with liquid nitrogen, He gas remains as a gas, and slips through the trap 130, whereas the radioisotope remains in the trap 130, for instance by solidifying. The radioisotope can be separated and extracted as a result.

In the radioisotope producing apparatus 100 the radioisotope can be separated and extracted in the trap 130 while the radiation beam goes on being projected. In the radioisotope producing apparatus 100, specifically, radiating of the radiation beam and extraction of the radiation isotope can be performed in parallel. When radiating of the radiation beam and extraction of the radiation isotope are parallel, either one of the processes of radiating of the radiation beam and extraction of the radiation isotope may be discontinued. The target element need not be removed from the crucible 202 at the time of extraction of the radioisotope. As a result, the radioisotope producing apparatus 100 allows generating radioisotopes efficiently.

(Variation)

Figure 12:
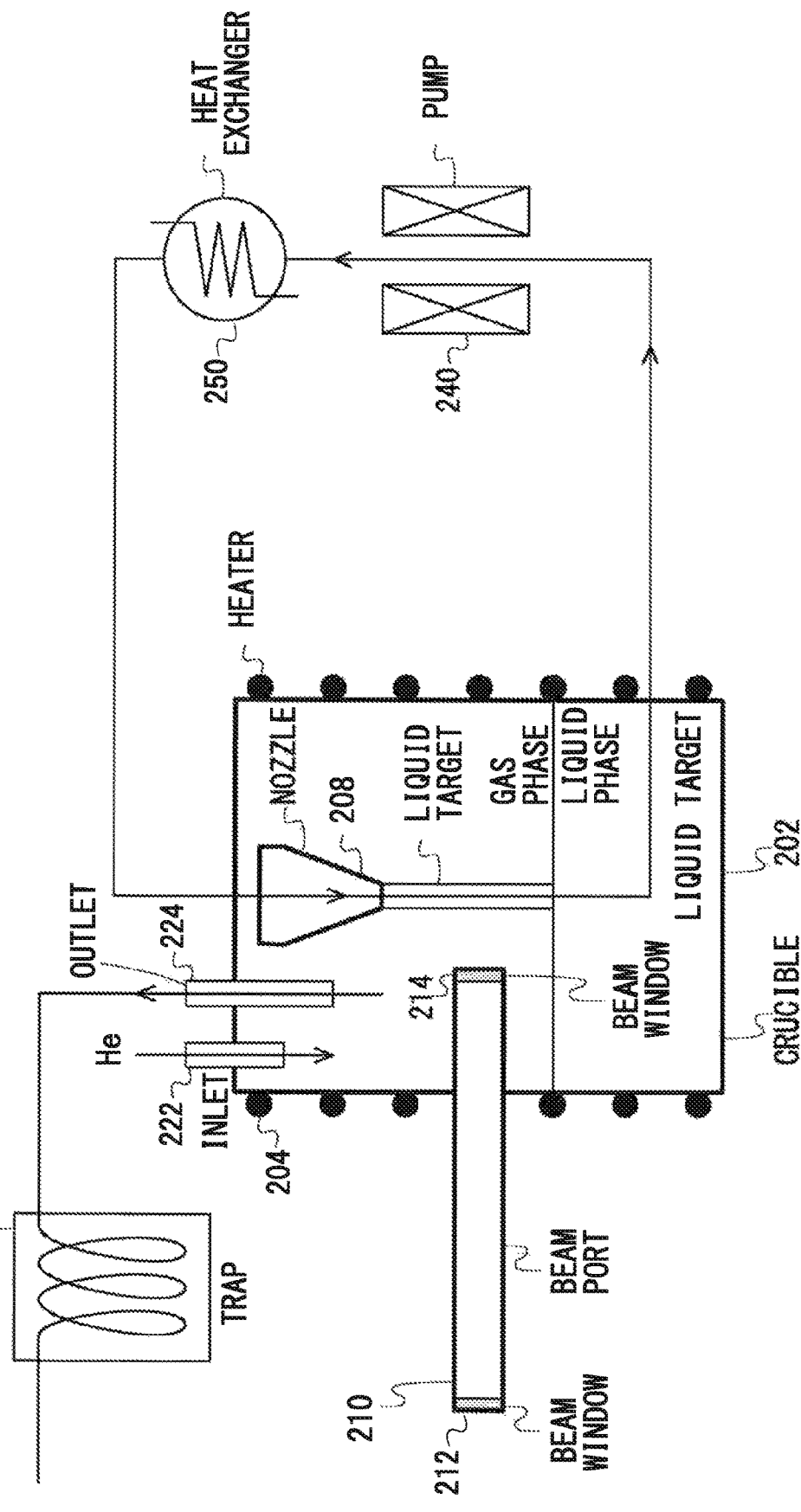
FIG. 12 is a diagram illustrating a configuration example of a radioisotope producing apparatus in a variation of the second embodiment.

FIG. 12 is a diagram illustrating a configuration example of a radioisotope producing apparatus of a variation of the present second embodiment. A radioisotope producing apparatus 200 in FIG. 4 has a crucible 202, a heater 204, a nozzle 208, a beam port 210, a beam window 212, a beam window 214, an inlet 222, an outlet 224, a trap 230, a pump 240 and a heat exchanger 250. The radioisotope producing apparatus 200 may have a jacket for cooling of the crucible 202, similarly to the radioisotope producing apparatus 100 in FIG. 11.

The crucible 202, the heater 204, the beam port 210, the beam window 212, the beam window 214, the inlet 222, the outlet 224 and the trap 230 have configurations identical to those of corresponding members of the radioisotope producing apparatus 100.

A passage for discharging a liquid target is provided at the bottom of the liquid phase of the crucible 202, such that a liquid target is discharged from the crucible 202 by the action of the pump 240. The discharged liquid target is cooled by the heat exchanger 250. The cooled liquid target is introduced into the nozzle 208 disposed at the top in the crucible 202. The liquid target introduced into the nozzle 208 flows in waterfall fashion from the bottom of the nozzle 208 and reaches the liquid phase of the crucible 202. The beam port 210 is installed so that the liquid target flowing out of the nozzle 208 is irradiated with a radiation beam. Heat generated by nuclear reactions can be efficiently removed and rises in the temperature in the crucible 202 can be suppressed, through forced circulation of the liquid target.

The radioisotope producing apparatus 200 operates in the same manner as the radioisotope producing apparatus 100, except for the portion in which the liquid target is forcibly caused to circulate.

(Action and Effect of the Second Embodiment)

Solid targets attached to an apparatus have conventionally been irradiated with a radiation beam, to generate a radioisotope within the solid target. In consequence, the solid target attached to the apparatus was removed after irradiation, and the radioisotope was extracted through dry distillation of the solid target, for instance by heating and dissolution. A time loss was thus incurred in the process from removal of the solid target until dry distillation was complete. Further, irradiation of a solid target necessitated herein curtailment of the irradiation output, so as to preclude melting of the solid target. Curtailing thus the output entails a reduction in the amount of generated radioisotope.

In the apparatus of the present second embodiment, by contrast, a liquid target is irradiated with a radiation beam, to generate a radioisotope within the liquid target. The proportion of the generated radioisotope that evaporates, relative to the element that evaporates from the liquid phase, can be increased through proper adjustment of temperature and pressure in the vicinity of the liquid surface of the liquid target. In the above example, the saturated vapor pressure of $^{211}$At is much higher than the saturated vapor pressure of Bi, and hence $^{211}$At makes up most of the elements that evaporate from the liquid phase. Accordingly, the radioisotope is purified through recovery of the evaporated element. The process of generation, separation, and purification of the radioisotope proceeds spontaneously until the partial pressure of $^{211}$At in the vicinity of the liquid surface of the liquid target reaches a saturated vapor pressure and an equilibrium state is attained. Therefore, $^{211}$At can go on being produced, continuously or intermittently, if At is extracted continuously or at appropriate timings. In the apparatus of the present second embodiment the radioisotope can be extracted without discontinuation of irradiating of the liquid target with the radiation beam, and without removal of the liquid target, and hence producing of the radioisotope, from generation up to extraction, can be accomplished in a shorter time. That is, the apparatus of the present second embodiment allows extracting a radiation isotope from a gas that contains an evaporated radiation isotope generated through irradiation with a radiation beam.

In the apparatus of the present second embodiment the target is a liquid, and accordingly it is not necessary to suppress the output of irradiation so as to preclude melting of the target, and the irradiation output of the radiation beam can be kept large, without rises in the temperature of the liquid target, through cooling of the liquid target for instance by convection or forced circulation. A greater amount of radioisotope can be produced by increasing the irradiation output.

Examples have been explained, in the above embodiments and variations, of an instance where bismuth (Bi) is used as the target substance and a-beams are used as the radiation beam that irradiates the target substance, to thereby generate $^{211}$At as a radioisotope. In the above embodiments and variations, however, a metal other than bismuth (Bi) may be used as the target substance, a radiation beam other than a-beams may be used to irradiate the target substance, and a radioisotope other than $^{211}$At may be generated.

The tables below set out combination patterns of target substances, radiation beams and radioisotopes that can be used in the above embodiments and variations.

TABLE 1

| | TARGET | | | | PRODUCT | | |
|---|---|---|---|---|---|---|---|
| No. | ATOMIC NUMBER | ELEMENT | MASS NUMBER | NUCLEAR REACTION | ATOMIC NUMBER | ELEMENT | MASS NUMBER |
| 1 | 16 | S | 34 | p, n | 17 | Cl | 34 m |
| 2 | 16 | S | 34 | α, n | 18 | Ar | 37 |
| 3 | 31 | Ga | 69 | α, n | 33 | As | 72 |
| 4 | 31 | Ga | 69 | α, 2n | 33 | As | 71 |
| 5 | 31 | Ga | 69 | α, 3n | 33 | As | 70 |
| 6 | 31 | Ga | 69 | 7Li, d | 33 | As | 74 |
| 7 | 31 | Ga | 71 | α, n | 33 | As | 74 |
| 3 | 31 | Ga | 71 | α, 2n | 33 | As | 73 |
| 9 | 31 | Ga | 71 | α, 3n | 33 | As | 72 |
| 10 | 31 | Ga | 71 | 7Li, p | 33 | As | 77 |
| 11 | 31 | Ga | 71 | 7Li, d | 33 | As | 76 |
| 12 | 34 | Se | 74 | p, n | 35 | Br | 74 |
| 13 | 34 | Se | 74 | α, n | 36 | Kr | 77 |
| 14 | 34 | Se | 74 | α, 2n | 36 | Kr | 76 |
| 15 | 34 | Se | 74 | α, 3n | 36 | Kr | 75 |
| 16 | 34 | Se | 76 | p, n | 35 | Br | 76 |
| 17 | 34 | Se | 76 | p, 2n | 35 | Br | 75 |
| 18 | 34 | Se | 76 | p, 3n | 35 | Br | 74 |
| 19 | 34 | Se | 76 | α, n | 36 | Kr | 79 |
| 20 | 34 | Se | 76 | α, 3n | 36 | Kr | 77 |
| 21 | 34 | Se | 77 | p, n | 35 | Br | 77 |
| 22 | 34 | Se | 77 | p, 2n | 35 | Br | 76 |
| 23 | 34 | Se | 77 | p, 3n | 35 | Br | 75 |
| 24 | 34 | Se | 77 | α, 2n | 36 | Kr | 79 |
| 25 | 34 | Se | 78 | p, 2n | 35 | Br | 77 |
| 26 | 34 | Se | 78 | p, 3n | 35 | Br | 76 |
| 27 | 34 | Se | 78 | α, 3n | 36 | Kr | 79 |
| 28 | 34 | Se | 80 | p, n | 35 | Br | 80 |
| 29 | 34 | Se | 80 | p, n | 35 | Br | 80 m |
| 30 | 34 | Se | 80 | p, 3n | 35 | Br | 78 |

| | | DESCENDANT NUCLIDE(S) | | HEATING TEMPERATURE | | | |
| | | | | 350° C. | | 650° C. | |
| No. | HALF-LIFE | 1 | 2 | TARGET | PRODUCT | TARGET | PRODUCT |
|---|---|---|---|---|---|---|---|
| 1 | 31.99 m | | | Liq. | Gas | Gas | Gas |
| 2 | 35.01 d | | | Liq. | Gas | Gas | Gas |
| 3 | 26.0 h | | | Liq. | Sol. | Liq. | Gas |
| 4 | 65.30 h | Ge-71 | | Liq. | Sol. | Liq. | Gas |
| 5 | 52.6 m | | | Liq. | Sol. | Liq. | Gas |
| 6 | 17.77 d | | | Liq. | Sol. | Liq. | Gas |

TABLE 1-continued

|   | | | | | | |
|---|---|---|---|---|---|---|
| 7 | 17.77 d | | | Liq. | Sol. | Liq. | Gas |
| 3 | 80.30 d | | | Liq. | Sol. | Liq. | Gas |
| 9 | 26.0 h | | | Liq. | Sol. | Liq. | Gas |
| 10 | 38.79 h | | | Liq. | Sol. | Liq. | Gas |
| 11 | 26.24 h | | | Liq. | Sol. | Liq. | Gas |
| 12 | 25.4 m | | | Liq. | Gas | Liq. | Gas |
| 13 | 74.4 m | Br-77 | | Liq. | Gas | Liq. | Gas |
| 14 | 14.8 h | Br-76 | | Liq. | Gas | Liq. | Gas |
| 15 | 4.60 m | Br-75 | Se-75 | Liq. | Gas | Liq. | Gas |
| 16 | 16.1 h | | | Liq. | Gas | Liq. | Gas |
| 17 | 96.7 m | Se-75 | | Liq. | Gas | Liq. | Gas |
| 18 | 25.4 m | | | Liq. | Gas | Liq. | Gas |
| 19 | 35.04 h | | | Liq. | Gas | Liq. | Gas |
| 20 | 74.4 m | Br-77 | | Liq. | Gas | Liq. | Gas |
| 21 | 57.04 h | | | Liq. | Gas | Liq. | Gas |
| 22 | 16.1 h | | | Liq. | Gas | Liq. | Gas |
| 23 | 96.7 m | Se-75 | | Liq. | Gas | Liq. | Gas |
| 24 | 35.04 h | | | Liq. | Gas | Liq. | Gas |
| 25 | 57.04 h | | | Liq. | Gas | Liq. | Gas |
| 26 | 16.1 h | | | Liq. | Gas | Liq. | Gas |
| 27 | 35.04 h | | | Liq. | Gas | Liq. | Gas |
| 28 | 17.68 m | | | Liq. | Gas | Liq. | Gas |
| 29 | 4.42 h | | | Liq. | Gas | Liq. | Gas |
| 30 | 6.45 m | | | Liq. | Gas | Liq. | Gas |

TABLE 2

| | TARGET | | | | PRODUCT | | |
|---|---|---|---|---|---|---|---|
| No. | ATOMIC NUMBER | ELEMENT | MASS NUMBER | NUCLEAR REACTION | ATOMIC NUMBER | ELEMENT | MASS NUMBER |
| 31 | 34 | Se | 80 | α, n | 36 | Kr | 83 m |
| 32 | 34 | Se | 82 | p, n | 35 | Br | 82 |
| 33 | 34 | Se | 82 | p, 3n | 35 | Br | 80 |
| 34 | 34 | Se | 82 | p, 3n | 35 | Br | 80 m |
| 35 | 34 | Se | 82 | α, n | 36 | Kr | 85 |
| 36 | 50 | Sn | 112 | 7Li, 3n | 53 | I | 116 |
| 37 | 50 | Sn | 112 | 7Li, 4n | 53 | I | 115 |
| 38 | 50 | Sn | 112 | 7Li, 5n | 53 | I | 114 |
| 39 | 50 | Sn | 112 | 7Li, 6n | 53 | I | 113 |
| 40 | 50 | Sn | 112 | 7Li, 7n | 53 | I | 112 |
| 41 | 50 | Sn | 112 | 7Li, 8n | 53 | I | 111 |
| 42 | 50 | Sn | 112 | 7Li, 9n | 53 | I | 110 |
| 43 | 50 | Sn | 114 | 7Li, 3n | 53 | I | 118 |
| 44 | 50 | Sn | 114 | 7Li, 4n | 53 | I | 117 |
| 45 | 50 | Sn | 114 | 7Li, 5n | 53 | I | 116 |
| 46 | 50 | Sn | 114 | 7Li, 6n | 53 | I | 115 |
| 47 | 50 | Sn | 114 | 7Li, 7n | 53 | I | 114 |
| 48 | 50 | Sn | 114 | 7Li, 8n | 53 | I | 113 |
| 49 | 50 | Sn | 114 | 7Li, 9n | 53 | I | 112 |
| 50 | 50 | Sn | 114 | 7Li, 6Li | 53 | I | 115 |
| 51 | 50 | Sn | 115 | 7Li, 3n | 53 | I | 119 |
| 52 | 50 | Sn | 115 | 7Li, 4n | 53 | I | 118 |
| 53 | 50 | Sn | 115 | 7Li, 5n | 53 | I | 117 |
| 54 | 50 | Sn | 115 | 7Li, 6n | 53 | I | 116 |
| 55 | 50 | Sn | 115 | 7Li, 7n | 53 | I | 115 |
| 56 | 50 | Sn | 115 | 7Li, 8n | 53 | I | 114 |
| 57 | 50 | Sn | 115 | 7Li, 9n | 53 | I | 113 |
| 58 | 50 | Sn | 116 | 7Li, 3n | 53 | I | 120 |
| 59 | 50 | Sn | 116 | 7Li, 3n | 53 | I | 120 m |
| 60 | 50 | Sn | 116 | 7Li, 4n | 53 | I | 119 |

| | | DESCENDANT | | HEATING TEMPERATURE | | | |
|---|---|---|---|---|---|---|---|
| | | NUCLIDE(S) | | 350° C. | | 650° C. | |
| No. | HALF-LIFE | 1 | 2 | TARGET | PRODUCT | TARGET | PRODUCT |
| 31 | 1.83 h | | | Liq. | Gas | Liq. | Gas |
| 32 | 35.3 h | | | Liq. | Gas | Liq. | Gas |
| 33 | 17.68 m | | | Liq. | Gas | Liq. | Gas |
| 34 | 4.42 h | | | Liq. | Gas | Liq. | Gas |
| 35 | 10.74 y | | | Liq. | Gas | Liq. | Gas |
| 36 | 2.91 s | Te-116 | Sb-116 | Liq. | Gas | Liq. | Gas |
| 37 | 1.3 m | Te-115 | Sb-115 | Liq. | Gas | Liq. | Gas |
| 38 | 2.1 s | Te-114 | Sb-114 | Liq. | Gas | Liq. | Gas |

TABLE 2-continued

| | | | | 350° C. | | 650° C. | |
|---|---|---|---|---|---|---|---|
| | | | | TARGET | PRODUCT | TARGET | PRODUCT |
| 39 | 6.6 s | Te-113 | Sb-113 | Liq. | Gas | Liq. | Gas |
| 40 | 3.34 s | Te-112 | Sb-112 | Liq. | Gas | Liq. | Gas |
| 41 | 2.5 s | Te-111 | Sb-111 | Liq. | Gas | Liq. | Gas |
| 42 | 664 ms | Te-110 | Sb-110 | Liq. | Gas | Liq. | Gas |
| 43 | 13.7 m | Te-118 | | Liq. | Gas | Liq. | Gas |
| 44 | 2.22 m | Te-117 | Sb-117 | Liq. | Gas | Liq. | Gas |
| 45 | 2.91 s | Te-116 | Sb-116 | Liq. | Gas | Liq. | Gas |
| 46 | 1.3 m | Te-115 | Sb-115 | Liq. | Gas | Liq. | Gas |
| 47 | 2.1 s | Te-114 | Sb-114 | Liq. | Gas | Liq. | Gas |
| 48 | 6.6 s | Te-113 | Sb-113 | Liq. | Gas | Liq. | Gas |
| 49 | 3.34 s | Te-112 | Sb-112 | Liq. | Gas | Liq. | Gas |
| 50 | 1.3 m | Te-115 | Sb-115 | Liq. | Gas | Liq. | Gas |
| 51 | 19.1 m | Te-119 | Sb-119 | Liq. | Gas | Liq. | Gas |
| 52 | 13.7 m | Te-118 | | Liq. | Gas | Liq. | Gas |
| 53 | 2.22 m | Te-117 | Sb-117 | Liq. | Gas | Liq. | Gas |
| 54 | 2.91 s | Te-116 | Sb-116 | Liq. | Gas | Liq. | Gas |
| 55 | 1.3 m | Te-115 | Sb-115 | Liq. | Gas | Liq. | Gas |
| 56 | 2.1 s | Te-114 | Sb-114 | Liq. | Gas | Liq. | Gas |
| 57 | 6.6 s | Te-113 | Sb-113 | Liq. | Gas | Liq. | Gas |
| 58 | 81.6 m | Sb-120 | | Liq. | Gas | Liq. | Gas |
| 59 | 53 m | Sb-120 | | Liq. | Gas | Liq. | Gas |
| 60 | 19.1 m | Te-119 | Sb-119 | Liq. | Gas | Liq. | Gas |

TABLE 3

| | TARGET | | | | PRODUCT | | |
|---|---|---|---|---|---|---|---|
| No. | ATOMIC NUMBER | ELEMENT | MASS NUMBER | NUCLEAR REACTION | ATOMIC NUMBER | ELEMENT | MASS NUMBER |
| 61 | 50 | Sn | 116 | 7Li, 5n | 53 | I | 118 |
| 62 | 50 | Sn | 116 | 7Li, 6n | 53 | I | 117 |
| 63 | 50 | Sn | 116 | 7Li, 7n | 53 | I | 116 |
| 64 | 50 | Sn | 116 | 7Li, 8n | 53 | I | 115 |
| 65 | 50 | Sn | 116 | 7Li, 9n | 53 | I | 114 |
| 66 | 50 | Sn | 117 | 7Li, 3n | 53 | I | 121 |
| 67 | 50 | Sn | 117 | 7Li, 4n | 53 | I | 120 |
| 68 | 50 | Sn | 117 | 7Li, 4n | 53 | I | 120 m |
| 69 | 50 | Sn | 117 | 7Li, 5n | 53 | I | 119 |
| 70 | 50 | Sn | 117 | 7Li, 6n | 53 | I | 118 |
| 71 | 50 | Sn | 117 | 7Li, 7n | 53 | I | 117 |
| 72 | 50 | Sn | 117 | 7Li, 8n | 53 | I | 116 |
| 73 | 50 | Sn | 117 | 7Li, 9n | 53 | I | 115 |
| 74 | 50 | Sn | 118 | 7Li, 4n | 53 | I | 121 |
| 75 | 50 | Sn | 118 | 7Li, 5n | 53 | I | 120 |
| 76 | 50 | Sn | 118 | 7Li, 5n | 53 | I | 120 m |
| 77 | 50 | Sn | 113 | 7Li, 6n | 53 | I | 119 |
| 78 | 50 | Sn | 113 | 7Li, 7n | 53 | I | 118 |
| 79 | 50 | Sn | 118 | 7Li, 8n | 53 | I | 117 |
| 80 | 50 | Sn | 118 | 7Li, 9n | 53 | I | 116 |
| 81 | 50 | Sn | 119 | 7Li, 3n | 53 | I | 123 |
| 82 | 50 | Sn | 119 | 7Li, 5n | 53 | I | 121 |
| 83 | 50 | Sn | 119 | 7Li, 6n | 53 | I | 120 |
| 84 | 50 | Sn | 119 | 7Li, 6n | 53 | I | 120 m |
| 85 | 50 | Sn | 119 | 7Li,7n | 53 | I | 119 |
| 86 | 50 | Sn | 119 | 7Li, 8n | 53 | I | 118 |
| 87 | 50 | Sn | 119 | 7Li, 9n | 53 | I | 117 |
| 88 | 50 | Sn | 120 | 7Li, 3n | 53 | I | 124 |
| 89 | 50 | Sn | 120 | 7Li, 4n | 53 | I | 123 |
| 90 | 50 | Sn | 120 | 7Li, 6n | 53 | I | 121 |

| | | DESCENDANT | | HEATING TEMPERATURE | | | |
|---|---|---|---|---|---|---|---|
| | | NUCLIDE(S) | | 350° C. | | 650° C. | |
| No. | HALF-LIFE | 1 | 2 | TARGET | PRODUCT | TARGET | PRODUCT |
| 61 | 13.7 m | Te-118 | | Liq. | Gas | Liq. | Gas |
| 62 | 2.22 m | Te-117 | Sb-117 | Liq. | Gas | Liq. | Gas |
| 63 | 2.91 s | Te-116 | Sb-116 | Liq. | Gas | Liq. | Gas |
| 64 | 1.3 m | Te-115 | Sb-115 | Liq. | Gas | Liq. | Gas |
| 65 | 2.1 s | Te-114 | Sb-114 | Liq. | Gas | Liq. | Gas |
| 66 | 2.12 h | Te-121 | | Liq. | Gas | Liq. | Gas |
| 67 | 81.6 m | Sb-120 | | Liq. | Gas | Liq. | Gas |
| 68 | 53 m | Sb-120 | | Liq. | Gas | Liq. | Gas |
| 69 | 19.1 m | Te-119 | Sb-119 | Liq. | Gas | Liq. | Gas |
| 70 | 13.7 m | Te-118 | | Liq. | Gas | Liq. | Gas |

TABLE 3-continued

| No. | Half-life | | | 350° C. TARGET | 350° C. PRODUCT | 650° C. TARGET | 650° C. PRODUCT |
|---|---|---|---|---|---|---|---|
| 71 | 2.22 m | Te-117 | Sb-117 | Liq. | Gas | Liq. | Gas |
| 72 | 2.91 s | Te-116 | Sb-116 | Liq. | Gas | Liq. | Gas |
| 73 | 1.3 m | Te-115 | Sb-115 | Liq. | Gas | Liq. | Gas |
| 74 | 2.12 h | Te-121 | | Liq. | Gas | Liq. | Gas |
| 75 | 81.6 m | Sb-120 | | Liq. | Gas | Liq. | Gas |
| 76 | 53 m | Sb-120 | | Liq. | Gas | Liq. | Gas |
| 77 | 19.1 m | Te-119 | Sb-119 | Liq. | Gas | Liq. | Gas |
| 78 | 13.7 m | Te-118 | | Liq. | Gas | Liq. | Gas |
| 79 | 2.22 m | Te-117 | Sb-117 | Liq. | Gas | Liq. | Gas |
| 80 | 2.91 s | Te-116 | Sb-116 | Liq. | Gas | Liq. | Gas |
| 81 | 13.22 h | | | Liq. | Gas | Liq. | Gas |
| 82 | 2.12 h | Te-121 | | Liq. | Gas | Liq. | Gas |
| 83 | 81.6 m | Sb-120 | | Liq. | Gas | Liq. | Gas |
| 84 | 53 m | Sb-120 | | Liq. | Gas | Liq. | Gas |
| 85 | 19.1 m | Te-119 | Sb-119 | Liq. | Gas | Liq. | Gas |
| 86 | 13.7 m | Te-118 | | Liq. | Gas | Liq. | Gas |
| 87 | 2.22 m | Te-117 | Sb-117 | Liq. | Gas | Liq. | Gas |
| 88 | 4.17 d | | | Liq. | Gas | Liq. | Gas |
| 89 | 13.22 h | | | Liq. | Gas | Liq. | Gas |
| 90 | 2.12 h | Te-121 | | Liq. | Gas | Liq. | Gas |

TABLE 4

| | TARGET | | | | PRODUCT | | |
|---|---|---|---|---|---|---|---|
| No. | ATOMIC NUMBER | ELEMENT | MASS NUMBER | NUCLEAR REACTION | ATOMIC NUMBER | ELEMENT | MASS NUMBER |
| 91 | 50 | Sn | 120 | 7Li, 7n | 53 | I | 120 |
| 92 | 50 | Sn | 120 | 7Li, 7n | 53 | I | 120 m |
| 93 | 50 | Sn | 120 | 7Li, 8n | 53 | I | 119 |
| 94 | 50 | Sn | 120 | 7Li, 9n | 53 | I | 118 |
| 95 | 50 | Sn | 122 | 7Li, 3n | 53 | I | 126 |
| 96 | 50 | Sn | 122 | 7Li, 4n | 53 | I | 125 |
| 97 | 50 | Sn | 122 | 7Li, 5n | 53 | I | 124 |
| 98 | 50 | Sn | 122 | 7Li, 6n | 53 | I | 123 |
| 99 | 50 | Sn | 122 | 7Li, 8n | 53 | I | 121 |
| 100 | 50 | Sn | 122 | 7Li, 9n | 53 | I | 120 |
| 101 | 50 | Sn | 122 | 7Li, 9n | 53 | I | 120 m |
| 102 | 51 | Sb | 121 | α, n | 53 | I | 124 |
| 103 | 51 | Sb | 121 | α, 2n | 53 | I | 123 |
| 104 | 51 | Sb | 121 | 7Li, 3n | 54 | Xe | 125 |
| 105 | 51 | Sb | 121 | 7Li, 5n | 54 | Xe | 123 |
| 106 | 51 | Sb | 121 | 7Li, 6n | 54 | Xe | 122 |
| 107 | 51 | Sb | 121 | 7Li, 7n | 54 | Xe | 121 |
| 108 | 51 | Sb | 121 | 7Li, 8n | 54 | Xe | 120 |
| 109 | 51 | Sb | 121 | 7Li, d | 53 | I | 126 |
| 110 | 51 | Sb | 123 | α, n | 53 | I | 126 |
| 111 | 51 | Sb | 123 | α, 2n | 53 | I | 125 |
| 112 | 51 | Sb | 123 | α, 3n | 53 | I | 124 |
| 113 | 51 | Sb | 123 | 7Li, 3n | 54 | Xe | 127 |
| 114 | 51 | Sb | 123 | 7Li, 5n | 54 | Xe | 125 |
| 115 | 51 | Sb | 123 | 7Li, 7n | 54 | Xe | 123 |
| 116 | 51 | Sb | 123 | 7Li, 8n | 54 | Xe | 122 |
| 117 | 51 | Sb | 123 | 7Li, 9n | 54 | Xe | 121 |
| 118 | 51 | Sb | 123 | 7Li, p | 53 | I | 129 |
| 119 | 51 | Sb | 123 | 7Li, d | 53 | I | 128 |
| 120 | 52 | Te | 120 | p, n | 53 | I | 120 |

| | | DESCENDANT NUCLIDE(S) | | HEATING TEMPERATURE 350° C. | | HEATING TEMPERATURE 650° C. | |
|---|---|---|---|---|---|---|---|
| No. | HALF-LIFE | 1 | 2 | TARGET | PRODUCT | TARGET | PRODUCT |
| 91 | 81.6 m | Sb-120 | | Liq. | Gas | Liq. | Gas |
| 92 | 53 m | Sb-120 | | Liq. | Gas | Liq. | Gas |
| 93 | 19.1 m | Te-119 | Sb-119 | Liq. | Gas | Liq. | Gas |
| 94 | 13.7 m | Te-118 | | Liq. | Gas | Liq. | Gas |
| 95 | 12.93 d | | | Liq. | Gas | Liq. | Gas |
| 96 | 59.4 d | | | Liq. | Gas | Liq. | Gas |
| 97 | 4.17 d | | | Liq. | Gas | Liq. | Gas |
| 98 | 13.22 h | | | Liq. | Gas | Liq. | Gas |
| 99 | 2.12 h | Te-121 | | Liq. | Gas | Liq. | Gas |
| 100 | 81.6 m | Sb-120 | | Liq. | Gas | Liq. | Gas |
| 101 | 53 m | Sb-120 | | Liq. | Gas | Liq. | Gas |
| 102 | 4.17 d | | | Sol. | Gas | Liq. | Gas |

TABLE 4-continued

| No. | Half-life | Descendant Nuclide 1 | 350° C. Target | 350° C. Product | 650° C. Target | 650° C. Product |
|---|---|---|---|---|---|---|
| 103 | 13.22 h | | Sol. | Gas | Liq. | Gas |
| 104 | 16.9 h | | Sol. | Gas | Liq. | Gas |
| 105 | 2.08 h | | Sol. | Gas | Liq. | Gas |
| 106 | 20.1 h | | Sol. | Gas | Liq. | Gas |
| 107 | 40.1 m | | Sol. | Gas | Liq. | Gas |
| 108 | 40 m | | Sol. | Gas | Liq. | Gas |
| 109 | 12.93 d | | Sol. | Gas | Liq. | Gas |
| 110 | 12.93 d | | Sol. | Gas | Liq. | Gas |
| 111 | 59.4 d | | Sol. | Gas | Liq. | Gas |
| 112 | 4.17 d | | Sol. | Gas | Liq. | Gas |
| 113 | 36.4 d | | Sol. | Gas | Liq. | Gas |
| 114 | 16.9 h | | Sol. | Gas | Liq. | Gas |
| 115 | 2.08 h | | Sol. | Gas | Liq. | Gas |
| 116 | 20.1 h | | Sol. | Gas | Liq. | Gas |
| 117 | 40.1 m | | Sol. | Gas | Liq. | Gas |
| 118 | 1.57e7 y | | Sol. | Gas | Liq. | Gas |
| 119 | 25.0 m | | Sol. | Gas | Liq. | Gas |
| 120 | 81.6 m | Sb-120 | Sol. | Gas | Liq. | Gas |

TABLE 5

| | TARGET | | | | PRODUCT | | |
|---|---|---|---|---|---|---|---|
| No. | ATOMIC NUMBER | ELEMENT | MASS NUMBER | NUCLEAR REACTION | ATOMIC NUMBER | ELEMENT | MASS NUMBER |
| 121 | 52 | Te | 120 | p, n | 53 | I | 120 m |
| 122 | 52 | Te | 120 | p, 2n | 53 | I | 119 |
| 123 | 52 | Te | 120 | p, 3n | 53 | I | 118 |
| 124 | 52 | Te | 120 | α, n | 54 | Xe | 123 |
| 125 | 52 | Te | 120 | α, 2n | 54 | Xe | 122 |
| 126 | 52 | Te | 120 | α, 3n | 54 | Xe | 121 |
| 127 | 52 | Te | 122 | p, 2n | 53 | I | 121 |
| 128 | 52 | Te | 122 | p, 3n | 53 | I | 120 |
| 129 | 52 | Te | 122 | p, 3n | 53 | I | 120 m |
| 130 | 52 | Te | 122 | α, n | 54 | Xe | 125 |
| 131 | 52 | Te | 122 | α, 3n | 54 | Xe | 123 |
| 132 | 52 | Te | 124 | p, n | 53 | I | 124 |
| 133 | 52 | Te | 124 | p, 2n | 53 | I | 123 |
| 134 | 52 | Te | 124 | α, n | 54 | Xe | 127 |
| 135 | 52 | Te | 124 | α, 3n | 54 | Xe | 125 |
| 136 | 52 | Te | 125 | p, n | 53 | I | 125 |
| 137 | 52 | Te | 125 | p, 2n | 53 | I | 124 |
| 138 | 52 | Te | 125 | p, 3n | 53 | I | 123 |
| 139 | 52 | Te | 125 | α, 2n | 54 | Xe | 127 |
| 140 | 52 | Te | 126 | p, n | 53 | I | 126 |
| 141 | 52 | Te | 126 | p, 2n | 53 | I | 125 |
| 142 | 52 | Te | 126 | p, 3n | 53 | I | 124 |
| 143 | 52 | Te | 126 | α, n | 54 | Xe | 129 m |
| 144 | 52 | Te | 126 | α, 3n | 54 | Xe | 127 |
| 145 | 52 | Te | 128 | p, n | 53 | I | 128 |
| 146 | 52 | Te | 128 | p, 3n | 53 | I | 126 |
| 147 | 52 | Te | 128 | α, n | 54 | Xe | 131 m |
| 148 | 52 | Te | 128 | α, 3n | 54 | Xe | 129 m |
| 149 | 52 | Te | 130 | p, n | 53 | I | 130 |
| 150 | 52 | Te | 130 | p, 2n | 53 | I | 129 |

| | | DESCENDANT NUCLIDE(S) | | HEATING TEMPERATURE | | | |
|---|---|---|---|---|---|---|---|
| | | | | 350° C. | | 650° C. | |
| No. | HALF-LIFE | 1 | 2 | TARGET | PRODUCT | TARGET | PRODUCT |
| 121 | 53 m | Sb-120 | | Sol. | Gas | Liq. | Gas |
| 122 | 19.1 m | Te-119 | Sb-119 | Sol. | Gas | Liq. | Gas |
| 123 | 13.7 m | Te-118 | | Sol. | Gas | Liq. | Gas |
| 124 | 2.08 h | | | Sol. | Gas | Liq. | Gas |
| 125 | 20.1 h | | | Sol. | Gas | Liq. | Gas |
| 126 | 40.1 m | | | Sol. | Gas | Liq. | Gas |
| 127 | 2.12 h | Te-121 | | Sol. | Gas | Liq. | Gas |
| 128 | 81.6 m | Sb-120 | | Sol. | Gas | Liq. | Gas |
| 129 | 53 m | Sb-120 | | Sol. | Gas | Liq. | Gas |
| 130 | 16.9 h | | | Sol. | Gas | Liq. | Gas |
| 131 | 2.08 h | | | Sol. | Gas | Liq. | Gas |
| 132 | 4.17 d | | | Sol. | Gas | Liq. | Gas |
| 133 | 13.22 h | | | Sol. | Gas | Liq. | Gas |
| 134 | 36.4 d | | | Sol. | Gas | Liq. | Gas |

TABLE 5-continued

| | | | | | |
|---|---|---|---|---|---|
| 135 16.9 h | | Sol. | Gas | Liq. | Gas |
| 136 59.4 d | | Sol. | Gas | Liq. | Gas |
| 137 4.17 d | | Sol. | Gas | Liq. | Gas |
| 138 13.22 h | | Sol. | Gas | Liq. | Gas |
| 139 36.4 d | | Sol. | Gas | Liq. | Gas |
| 140 12.93 d | | Sol. | Gas | Liq. | Gas |
| 141 59.4 d | | Sol. | Gas | Liq. | Gas |
| 142 4.17 d | | Sol. | Gas | Liq. | Gas |
| 143 8.88 d | | Sol. | Gas | Liq. | Gas |
| 144 36.4 d | | Sol. | Gas | Liq. | Gas |
| 145 25.0 m | | Sol. | Gas | Liq. | Gas |
| 146 12.93 d | | Sol. | Gas | Liq. | Gas |
| 147 11.84 d | | Sol. | Gas | Liq. | Gas |
| 148 8.88 d | | Sol. | Gas | Liq. | Gas |
| 149 12.36 h | | Sol. | Gas | Liq. | Gas |
| 150 1.57e7 y | | Sol. | Gas | Liq. | Gas |

TABLE 6

| | TARGET | | | | PRODUCT | | |
|---|---|---|---|---|---|---|---|
| No. | ATOMIC NUMBER | ELEMENT | MASS NUMBER | NUCLEAR REACTION | ATOMIC NUMBER | ELEMENT | MASS NUMBER |
| 151 | 52 | Te | 130 | p, 3n | 53 | I | 128 |
| 152 | 52 | Te | 130 | α, n | 54 | Xe | 133 |
| 153 | 52 | Te | 130 | α, n | 54 | Xe | 133 m |
| 154 | 82 | Pb | 204 | 7Li, 3n | 85 | At | 208 |
| 155 | 82 | Pb | 204 | 7Li, 4n | 85 | At | 207 |
| 156 | 82 | Pb | 204 | 7Li, 5n | 85 | At | 206 |
| 157 | 82 | Pb | 204 | 7Li, 6n | 85 | At | 205 |
| 153 | 82 | Pb | 204 | 7Li, 7n | 85 | At | 204 |
| 159 | 82 | Pb | 204 | 7Li, 8n | 85 | At | 203 |
| 160 | 82 | Pb | 204 | 7Li, p | 84 | Po | 210 |
| 161 | 82 | Pb | 204 | 7Li, d | 84 | Po | 209 |
| 162 | 82 | Pb | 206 | 7Li, 3n | 85 | At | 210 |
| 163 | 82 | Pb | 206 | 7Li, 4n | 85 | At | 209 |
| 164 | 82 | Pb | 206 | 7Li, 5n | 85 | At | 208 |
| 165 | 82 | Pb | 206 | 7Li, 6n | 85 | At | 207 |
| 166 | 82 | Pb | 206 | 7Li, 7n | 85 | At | 206 |
| 167 | 82 | Pb | 206 | 7Li, 8n | 85 | At | 205 |
| 168 | 82 | Pb | 206 | 7Li, 9n | 85 | At | 204 |
| 169 | 82 | Pb | 207 | 7Li, 3n | 85 | At | 211 |
| 170 | 82 | Pb | 207 | 7Li, 4n | 85 | At | 210 |
| 171 | 82 | Pb | 207 | 7Li, 5n | 85 | At | 209 |
| 172 | 82 | Pb | 207 | 7Li, 6n | 85 | At | 208 |
| 173 | 82 | Pb | 207 | 7Li, 7n | 85 | At | 207 |
| 174 | 82 | Pb | 207 | 7Li, 8n | 85 | At | 206 |
| 175 | 82 | Pb | 207 | 7Li, 9n | 85 | At | 205 |
| 176 | 82 | Pb | 208 | 7Li, 4n | 85 | At | 211 |
| 177 | 82 | Pb | 208 | 7Li, 5n | 85 | At | 210 |
| 178 | 82 | Pb | 208 | 7Li, 6n | 85 | At | 209 |
| 179 | 82 | Pb | 208 | 7Li, 7n | 85 | At | 208 |
| 18 0 | 82 | Pb | 208 | 7Li, 8n | 85 | At | 207 |

| | | DESCENDANT NUCLIDE(S) | | HEATING TEMPERATURE | | | |
|---|---|---|---|---|---|---|---|
| | | | | 350° C. | | 650° C. | |
| No. | HALF-LIFE | 1 | 2 | TARGET | PRODUCT | TARGET | PRODUCT |
| 151 | 25.0 m | | | Sol. | Gas | Liq. | Gas |
| 152 | 5.25 d | | | Sol. | Gas | Liq. | Gas |
| 153 | 2.2 d | | | Sol. | Gas | Liq. | Gas |
| 154 | 1.63 h | * | | Liq. | Gas | Liq. | Gas |
| 155 | 1.81 h | * | | Liq. | Gas | Liq. | Gas |
| 156 | 30.6 m | * | | Liq. | Gas | Liq. | Gas |
| 157 | 26.9 m | * | | Liq. | Gas | Liq. | Gas |
| 153 | 9.12 m | * | | Liq. | Gas | Liq. | Gas |
| 159 | 7.4 m | * | | Liq. | Gas | Liq. | Gas |
| 160 | 138.4 d | * | | Liq. | Gas | Liq. | Gas |
| 161 | 124 y | * | | Liq. | Gas | Liq. | Gas |
| 162 | 8.1 h | * | | Liq. | Gas | Liq. | Gas |
| 163 | 5.42 h | * | | Liq. | Gas | Liq. | Gas |
| 164 | 1.63 h | * | | Liq. | Gas | Liq. | Gas |
| 165 | 1.81 h | * | | Liq. | Gas | Liq. | Gas |
| 166 | 30.6 m | * | | Liq. | Gas | Liq. | Gas |
| 167 | 26.9 m | * | | Liq. | Gas | Liq. | Gas |

TABLE 6-continued

| 168 | 9.12 m | * | Liq. | Gas | Liq. | Gas |
| 169 | 7.214 h | * | Liq. | Gas | Liq. | Gas |
| 170 | 8.1 h | * | Liq. | Gas | Liq. | Gas |
| 171 | 5.42 h | * | Liq. | Gas | Liq. | Gas |
| 172 | 1.63 h | * | Liq. | Gas | Liq. | Gas |
| 173 | 1.81 h | * | Liq. | Gas | Liq. | Gas |
| 174 | 30.6 m | * | Liq. | Gas | Liq. | Gas |
| 175 | 26.9 m | * | Liq. | Gas | Liq. | Gas |
| 176 | 7.214 h | * | Liq. | Gas | Liq. | Gas |
| 177 | 8.1 h | * | Liq. | Gas | Liq. | Gas |
| 178 | 5.42 h | * | Liq. | Gas | Liq. | Gas |
| 179 | 1.63 h | * | Liq. | Gas | Liq. | Gas |
| 180 | 1.81 h | * | Liq. | Gas | Liq. | Gas |

TABLE 7

| | TARGET | | | | PRODUCT | | |
| --- | --- | --- | --- | --- | --- | --- | --- |
| No. | ATOMIC NUMBER | ELEMENT | MASS NUMBER | NUCLEAR REACTION | ATOMIC NUMBER | ELEMENT | MASS NUMBER |
| 181 | 82 | Pb | 208 | 7Li, 9n | 85 | At | 206 |
| 182 | 83 | Bi | 209 | α, 2n | 85 | At | 211 |
| 133 | 83 | Bi | 209 | α, 3n | 85 | At | 210 |
| 184 | 83 | Bi | 209 | 7Li, 3n | 86 | Rn | 213 |
| 185 | 83 | Bi | 209 | 7Li, 4n | 86 | Rn | 212 |
| 186 | 83 | Bi | 209 | 7Li, 5n | 86 | Rn | 211 |
| 187 | 83 | Bi | 209 | 7Li, 6n | 86 | Rn | 210 |
| 188 | 83 | Bi | 209 | 7Li, 7n | 86 | Rn | 209 |
| 189 | 83 | Bi | 209 | 7Li, 8n | 86 | Rn | 208 |
| 190 | 83 | Bi | 209 | 7Li, 9n | 86 | Rn | 207 |

| | | DESCENDANT NUCLIDE(S) | | HEATING TEMPERATURE | | | |
| --- | --- | --- | --- | --- | --- | --- | --- |
| | | | | 350° C. | | 650° C. | |
| No. | HALF-LIFE | 1 | 2 | TARGET | PRODUCT | TARGET | PRODUCT |
| 181 | 30.6 m | * | | Liq. | Gas | Liq. | Gas |
| 182 | 7.214 h | * | | Liq. | Gas | Liq. | Gas |
| 133 | 8.1 h | * | | Liq. | Gas | Liq. | Gas |
| 184 | 19.5 ms | * | | Liq. | Gas | Liq. | Gas |
| 185 | 23.9 m | * | | Liq. | Gas | Liq. | Gas |
| 186 | 14.6 h | * | | Liq. | Gas | Liq. | Gas |
| 187 | 2.4 h | * | | Liq. | Gas | Liq. | Gas |
| 188 | 28.8 m | * | | Liq. | Gas | Liq. | Gas |
| 189 | 24.3 m | * | | Liq. | Gas | Liq. | Gas |
| 190 | 9.25 m | * | | Liq. | Gas | Liq. | Gas |

The description in the column notated as "Target" in the above tables exemplifies elements that can be used as a target substance in the above embodiments and variations; as set out in the tables, the elements may be for instance sulfur (S), gallium (Ga), selenium (Se), tin (Sn), antimony (Sb), tellurium (Te), lead (Pb) and bismuth (Bi).

The description in the column notated as "nuclear reaction" in the above tables exemplifies the types of nuclear reaction elicited by the radiation beam that irradiates the target substance, in the above embodiments and variations; as set out in the tables, the nuclear reaction may be for instance an a-reaction using a-particles, a p reaction using protons, and a nuclear reaction using lithium. In the column of nuclear reaction, the descriptor to the left of the comma represents the particle that strikes the target substance, and the descriptor to the right of the comma represents the particle emitted by the target substance.

The description in the column "Progeny nuclide" in the tables denotes the nuclide that is generated through product decay. As set out in the tables, examples of progeny nuclides include germanium (Ge) and bromine (Br). Instances where a variety of progeny nuclides are generated that do not fit into the column of the tables are marked with an asterisk (*).

The descriptions in the column "Target" and column "Product" of the column notated as "Heating temperature" denote the state of the respective substance. The caption "Sol" denotes a solid state, "Liq" denotes a liquid state, and "Gas" denotes a gaseous state.

Various radioisotopes can be generated in the above embodiments and variations, as set out in the column "Product" of the tables, by utilizing the combinations of target and nuclear reaction given in the tables. In the above tables, the target denotes a substance the temperature of which, at the time of vaporization at the pressure upon irradiation with the radiation beam, is higher than the temperature at which the radioisotope, as the product, vaporizes under that same pressure. In the above embodiments and variations, therefore, a radioisotope can vaporize, without vaporization of the target substance, and can be extracted from the gas in the trap 130, by adjusting the temperature of the target substance so as to lie in a temperature range that is equal to or higher than the temperature at the time of vaporization of the radioisotope, under a same pressure, and that is lower than the temperature at the time of vaporization of the target substance under that same pressure. The term "vaporization" in the present application signifies that a substance that has reached a gaseous state and encompasses conceptually for instance a state resulting from transition to a gas phase by going beyond the boiling point or the sublimation point of that substance. Accordingly, the wording "temperature at the time of vaporization of a target substance, under a same pressure" can be rephrased as "boiling point or sublimation point at which a target substance evaporates, under a same pressure".

For instance in the combination No. 1 in the tables, the boiling point at normal pressure of sulfur (S) which is the target substance is about 444° C., whereas the boiling point at normal pressure of chlorine (CI) which is the product is about −34° C., lower than that of sulfur (S). Accordingly, if the target is irradiated with a radiation beam in a state where the temperature in the crucible 102 is 350° C., as indicated in the column "Heating temperature" of the tables, then sulfur (S) which is the target substance remains in a liquid state, while only chlorine (CI) which is the product evaporates in the crucible 102, the chlorine (CI) having evaporated in the crucible 102 being then condensed in the trap 130, to be extracted as a result.

For instance in the combinations No. 3 and No. 7 in the tables, the boiling point at normal pressure of gallium (Ga) which is the target substance is about 2400° C., whereas the boiling point at normal pressure of arsenic (As) which is the product is about 613° C., lower than that of gallium (Ga). Accordingly, if the target is irradiated with a radiation beam in a state where the temperature in the crucible 102 is 650° C., as indicated in the column "Heating temperature" of the tables, then gallium (Ga) which is the target substance remains in a liquid state, while only arsenic (As) which is the product evaporates in the crucible 102, the arsenic (As) having evaporated in the crucible 102 being then condensed in the trap 130, to be extracted as a result.

For instance in the combinations No. 12, No. 16 and No. 22 in the tables, the boiling point at normal pressure of selenium (Se) which is the target substance is about 684° C., whereas the boiling point at normal pressure of bromine (Br) which is the product is about 58° C., lower than that of selenium (Se). Accordingly if the target is irradiated with a radiation beam in a state where the temperature in the crucible 102 is 350° C. or 650° C., as indicated in the column "Heating temperature" of the tables, then selenium (Se) which is the target substance remains in a liquid state, while only bromine (Br) which is the product evaporates in the crucible 102, the bromine (Br) having evaporated in the crucible 102 being then condensed in the trap 130, to be extracted as a result.

For instance in the combinations No. 102 and No. 112 in the tables, the boiling point at normal pressure of antimony (Sb) which is the target substance is about 1587° C., whereas the boiling point at normal pressure of iodine (I) which is the product is about 148° C., lower than that of antimony (Sb). Accordingly, if the target is irradiated with a radiation beam is in a state where the temperature in the crucible 102 is 350° C. or 650° C., as indicated in the column "Heating temperature" of the tables, then antimony (Sb) which is the target substance remains in a solid or liquid state, while only iodine (I) which is the product evaporates in the crucible 102, the iodine (I) having evaporated in the crucible 102 being then condensed in the trap 130, to be extracted as a result.

For instance in the combination No. 186 in the tables, the boiling point at normal pressure of bismuth (Bi) which is the target substance is about 1564° C., whereas the boiling point at normal pressure of radon (Rn) which is the product is about −62° C., lower than that of bismuth (Bi). Accordingly if the target is irradiated with a radiation beam in a state where the temperature in the crucible 102 is 350° C. or 650° C., as indicated in the column "Heating temperature" of the tables, then bismuth (Bi) which is the target substance remains in a solid or liquid state, while only radon (Rn) which is the product evaporates in the crucible 102, the radon (Rn) having evaporated in the crucible 102 being then condensed in the trap 130, to be extracted as a result.

In the column "Heating temperature" of the tables, two instances, of temperature of 350° C. and 650° C. are illustrated. However, the temperature in the crucible 102, when a combination of target and nuclear reaction set out in the above tables is to be implemented in the above embodiments and variations, is not limited to either 350° C. or 650° C. The temperature of the target substance in the crucible 102, in a case where a combination of target and nuclear reaction set out in the tables above and to be implemented in the above embodiments and variations, is set to an arbitrary temperature within a temperature range that is equal to or higher than the temperature at the time of vaporization of the product under the pressure in the crucible 102 and that is lower than the temperature at the time of vaporization of the target substance under that same pressure. For instance in the combination No. 1 in the tables, the boiling point at normal pressure of sulfur (S) which is the target substance is about 444° C., whereas the boiling point at normal pressure of chlorine (CI) which is the product is about −34° C., lower than that of sulfur (S). Accordingly, assuming that the interior of the crucible 102 is at normal pressure, if the temperature of sulfur (S) in the crucible 102 lies in the range from about −30° C. to about 440° C. then just chlorine (CI), which is the product, can be allowed to evaporate in the crucible 102, without vaporization of sulfur (S) which is the target substance, whereupon the chlorine (CI) having evaporated in the crucible 102 can be extracted by being condensed in the trap 130.

The column "Target" in the above tables sets out only the name of the target-constituting element, but two or more types of target substance may be held in the crucible 102, or a substance other than a target may be present, along with the target substance, in the crucible 102, provided that a substance serving as a target, such as those in the column "Target" of the tables, is contained in the crucible 102.

In a case where an alloy is formed in the crucible 102 by charging two or more types of substance together, the melting point is different from that in a case where respective substance is present alone in the crucible 102. For instance, the melting point of an alloy produced at a 58:42 ratio of bismuth (Bi) and tin (Sn), at normal pressure, is 138° C. i.e. lower than 271° C., which is the melting point of bismuth (Bi), and lower than 232° C., which is the melting point of tin (Sn). However, the boiling point itself of a product obtained by irradiating bismuth (Bi) with a radiation beam and the boiling point itself of a product obtained by irradiating tin (Sn) with a radiation beam are unrelated, regardless of whether the foregoing are in an alloyed state or not, and accordingly the products can be extracted selectively in the trap 130, through adjustment of the interior of the crucible 102 to an appropriate temperature.

The above products can be used for diagnosis and treatment in medicine, and also in various applications other than medical purposes, such as quality management of agricultural products and industrial products. For instance, the above product can play a role as a tracer for observing the state, of a plant, resulting from migration of substances from a crop soil, or a role as a reagent for verifying a surface treatment state in an industrial product.

REFERENCE SIGNS LIST 1, 1A Radiolabeled compound producing apparatus
2, 2A Radioisotope producing apparatus
3 Synthesis apparatus
21 Crucible
21A Target container
21B Storage container
22, 22A, 22B Heater
23 Beam port
24 Gas introduction port
25 Gas lead-out port
26 Beam window
27 Beam window
28 Jacket
29 Transfer pipe
31 First column
32 Second column
100 Radioisotope producing apparatus
102 Crucible
104 Heater
106 Jacket
110 Beam port
112 Beam window
114 Beam window
122 Inlet
124 Outlet
130 Trap
200 Radioisotope producing apparatus
202 Crucible
204 Heater
208 Nozzle
210 Beam port
212 Beam window
214 Beam window
222 Inlet
224 Outlet
230 Trap
240 Pump
250 Heat exchanger

The invention claimed is:

1. A method for producing a radiolabeled compound, comprising the steps of:
A method for producing a radiolabeled compound, comprising the irradiating an alloy as a target substance with a radiation beam, to generate two or more radioisotopes from the alloy, and allowing the two or more radioisotopes to migrate into a gas;
generating an intermediate label by allowing a first radioisotope, from among the two or more radioisotopes having migrated into the gas, to react with a label precursor; and
generating a final label by allowing a second radioisotope different from the first radioisotope, from among the two or more radioisotopes having migrated into the gas, to react with the intermediate label.

2. A method for producing a radiolabeled compound, comprising the steps of:
irradiating an alloy of a target substance with a radiation beam, to generate two or more radioisotopes from the alloy, and allowing the two or more radioisotopes to migrate into a gas;
generating a first intermediate label by allowing a first radioisotope, from among the two or more radioisotopes having migrated into the gas, to react with a label precursor;
generating a second intermediate label by allowing a second radioisotope different from the first radioisotope, from among the two or more radioisotopes having migrated into the gas, to react with a label precursor; and
generating a final label by condensing the first intermediate label and the second intermediate label.

3. The method for producing a radiolabeled compound of claim 1, further comprising:
a step of adjusting the temperature of the alloy so as to be a temperature at which both the first radioisotope and the second radioisotope evaporate, during irradiation with the radiation beam.

4. An apparatus for producing a radiolabeled compound, comprising:
isotope generation means for irradiating an alloy as a target substance with a radiation beam, to generate two or more radioisotopes from the alloy, and allowing the two or more radioisotopes to migrate into a gas;
a first generating unit which generates an intermediate label by allowing a first radioisotope, from among the two or more radioisotopes having migrated into the gas, to react with a label precursor; and
a second generating unit which generates a final label by allowing a second radioisotope different from the first radioisotope, from among the two or more radioisotopes having migrated into the gas, to react with the intermediate label.

5. An apparatus for producing a radiolabeled compound, comprising:
isotope generation means for irradiating an alloy as a target substance with a radiation beam, to generate two or more radioisotopes from the alloy, and allowing the two or more radioisotopes to migrate into a gas;
a third generating unit which generates a first intermediate label by allowing a first radioisotope, from among the two or more radioisotopes having migrated into the gas, to react with a label precursor;
a fourth generating unit which generates a second intermediate label by allowing a second radioisotope different from the first radioisotope, from among the two or more radioisotopes having migrated into the gas, to react with a label precursor; and
a fifth generating unit which generates a final label through condensation of the first intermediate label and the second intermediate label.

6. The method for producing a radiolabeled compound of claim 2, further comprising:
a step of adjusting the temperature of the alloy so as to be a temperature at which both the first radioisotope and the second radioisotope evaporate, during irradiation with the radiation beam.

* * * * *

UNITED STATES PATENT AND TRADEMARK OFFICE
CERTIFICATE OF CORRECTION

PATENT NO. : 12,102,694 B2
APPLICATION NO. : 17/442715
DATED : October 1, 2024
INVENTOR(S) : Noriko Ishioka et al.

Page 1 of 1

It is certified that error appears in the above-identified patent and that said Letters Patent is hereby corrected as shown below:

In the Claims

At Column 35, Lines 48-49, "A method for producing a radiolabeled compound, comprising the irradiating" should be -- irradiating --.

Signed and Sealed this
Fourth Day of February, 2025

Coke Morgan Stewart
*Acting Director of the United States Patent and Trademark Office*